US011262362B2

(12) United States Patent
Wise et al.

(10) Patent No.: US 11,262,362 B2
(45) Date of Patent: Mar. 1, 2022

(54) 2-HYDROXYGLUTARATE AS A BIOMARKER FOR CHRONIC HYPOXIA

(71) Applicant: MEMORIAL SLOAN KETTERING CANCER CENTER, New York, NY (US)

(72) Inventors: David R. Wise, New York, NY (US); Patrick S. Ward, Cambridge, MA (US); Craig B. Thompson, New York, NY (US)

(73) Assignee: Memorial Sloan-Kettering Cancer Center, New York, NY (US)

( * ) Notice: Subject to any disclaimer, the term of this patent is extended or adjusted under 35 U.S.C. 154(b) by 0 days.

(21) Appl. No.: 14/359,074

(22) PCT Filed: Nov. 18, 2012

(86) PCT No.: PCT/US2012/065731
§ 371 (c)(1),
(2) Date: May 16, 2014

(87) PCT Pub. No.: WO2013/075065
PCT Pub. Date: May 23, 2013

(65) Prior Publication Data
US 2014/0314728 A1  Oct. 23, 2014

Related U.S. Application Data

(60) Provisional application No. 61/561,737, filed on Nov. 18, 2011.

(51) Int. Cl.
| | | |
|---|---|---|
| *G01N 33/68* | (2006.01) | |
| *A61K 31/522* | (2006.01) | |
| *A61K 35/19* | (2015.01) | |
| *C12Q 1/6881* | (2018.01) | |
| *G01N 33/53* | (2006.01) | |
| *A61K 33/00* | (2006.01) | |
| *A61K 35/18* | (2015.01) | |
| *C12Q 1/6883* | (2018.01) | |
| *G01N 30/72* | (2006.01) | |
| *H01J 49/00* | (2006.01) | |

(52) U.S. Cl.
CPC ....... *G01N 33/6893* (2013.01); *A61K 31/522* (2013.01); *A61K 33/00* (2013.01); *A61K 35/18* (2013.01); *A61K 35/19* (2013.01); *C12Q 1/6881* (2013.01); *C12Q 1/6883* (2013.01); *G01N 30/7206* (2013.01); *G01N 33/5308* (2013.01); *H01J 49/0036* (2013.01); *G01N 2800/7038* (2013.01)

(58) Field of Classification Search
CPC .......... G01N 33/6893; G01N 30/7206; G01N 33/5308; G01N 2800/7038; A61K 31/522; A61K 33/00; A61K 35/19; A61K 35/18; C12Q 1/6881; C12Q 1/6883; H01J 49/0036

USPC ....................................................... 424/93.73
See application file for complete search history.

(56) References Cited

U.S. PATENT DOCUMENTS

| | | |
|---|---|---|
| 10,450,596 B2 | 10/2019 | Intlekofer et al. |
| 2002/0192737 A1 | 12/2002 | Kaelin et al. |
| 2006/0084123 A1 | 4/2006 | Harris et al. |
| 2009/0186358 A1 | 7/2009 | Melville et al. |
| 2012/0202883 A1 | 8/2012 | Hai et al. |
| 2013/0109643 A1* | 5/2013 | Riggins et al. .............. 514/34 |
| 2013/0316385 A1 | 11/2013 | Cantley et al. |
| 2014/0067234 A1 | 3/2014 | Brown |
| 2016/0033533 A1 | 2/2016 | Wise et al. |
| 2017/0175164 A1 | 6/2017 | Intlekofer et al. |
| 2020/0032315 A1 | 1/2020 | Intlekofer et al. |

FOREIGN PATENT DOCUMENTS

| | | | |
|---|---|---|---|
| JP | 2013-506833 A | 2/2013 | |
| WO | WO-2004/046729 A2 | 6/2004 | |
| WO | WO2010/105243 * | 9/2010 | .............. C12Q 1/32 |
| WO | WO-2010/105243 A1 | 9/2010 | |
| WO | WO-2011/040874 A1 | 4/2011 | |
| WO | WO-2011/050211 A2 | 4/2011 | |
| WO | WO-2011/143160 A2 | 11/2011 | |
| WO | WO-2013/075065 A1 | 5/2013 | |
| WO | WO-2013/086365 A2 | 6/2013 | |

OTHER PUBLICATIONS

Wise et al. (Hypoxia promotes isocitrate dehydrogenase-dependent carboxylation of α-ketoglutarate to citrate to support cell growth and viability. PNAS, 108(49) 19611-19616; epublished Nov. 21, 2011).*

Struys et al. (Measurement of Urinary D- and L-2-Hydroxyglutarate Enantiomers by Stable-Isotope-Dilution Liquid Chromatography-Tandem Mass Spectrometry after Derivatization with Diacetyl-L-Tartaric Anhydride. Clinical Chemistry (2004) 50:8 1391-1395).*

(Continued)

*Primary Examiner* — Sharmila G Landau
*Assistant Examiner* — Natalie M Moss
(74) *Attorney, Agent, or Firm* — Wolf, Greenfield & Sacks, P.C.

(57) ABSTRACT

The present invention provides biomarkers for sensitive, specific, accurate and quantitative diagnosis and assessment of chronic hypoxia. In particular, the present invention provides 2-hydroxyglutarate as a biomarker that is differentially produced in chronic hypoxia. Furthermore, embodiments of the invention are able to differentiate between chronic and acute hypoxia. Assays for levels of 2-hydroxyglutarate may be used alone or in conjunction with additional biomarkers of hypoxia to increase the precision of analysis. In particular embodiments of the invention, the level of 2-hydroxyglutarate and at least one second biomarker may be assayed to generate a hypoxic profile that can be compared to a reference or control profile, thereby diagnosing a subject as normoxic, chronically hypoxic, or acutely hypoxic.

7 Claims, 5 Drawing Sheets

(56) References Cited

OTHER PUBLICATIONS

Brown et al. (Methods in Enzymology (2007) 35:295-321).*
Dang et al. (Cancer-associated IDH1 mutations produce-hydroxyglutarate. Nature Dec. 10, 2009: 462(7274): 1-18).*
Kohshi et al. (Radiotherapy after hyperbaric oxygenation for malignant gliomas: a pilot study. J. Cancer Res Clin Oncol (1996) 122:676-678).*
Kaur et al. (Hypoxia and the hypoxia-inducible-factor pathway in glioma growth and angiogenesis. Neuro-Oncology (2005) 134-153).*
Bristow et al. (Hypoxia, DNA repair and genetic instability. Nature Reviews. 2008 vol. 8, 180-192).*
Haacke et al. (Observing Tumor Vascularity Non-Invasively Using Magnetic Resonance Imaging. Anal Stereol 2002;21:107-113).*
Steenweg et al. (L-2-Hydroxyglutaric Aciduria: Pattern of MR Imaging Abnormalities in 56 Patients. Radiology 251(3) 2009).*
Seijo-Martinez et al. (L-2-Hydroxyglutaric Aciduria Clinical, Neuroimaging, and Neuropathological Findings Arch Neurol. 2005;62(4):666-670).*
Bethesda Hyerpbaric Oxygen Therapy (Epilepsy—Bethesda Hyperbaric Oxygen Therapy. Apr. 2009, pp. 1-3).*
Delaney et al. (How Can Hyperbaric Oxygen Contribute to Treatment. The Physician and Sports Medicine 29(3) 2001) pp. 1-8).*
Sytsma et al. (The Basics of Experimental Design [A Quick and Non-Technical Guide] 2009 pp. 1-11).*
Intlekofer et al. (Hypoxia Induces Production of L-2-Hydroxyglutarate. Cell Metab. Aug. 4, 2015; 22(2): 304-311).*
Chang, C. M. et al., The Role of Isocitrate Dehydrogenase Mutations in Glioma Brain Tumors, Molecular Targets of CNS Tumors, pp. 413-436 (2011).
International Search Report for PCT/US2012/065731, 2 pages (dated Feb. 8, 2013).
Metellus, P. et al., IDH mutation status impact on in vivo hypoxia biomarkers expression: new insights from a clinical, nuclear imaging and immunohistochemical study in 33 glioma patients, J. Neurooncol., 105(3):591-600 (2011).
Partial Supplementary European Search Report for 12850119.4, 5 pages (dated Apr. 21, 2015).
Wise, D.R. et al., Hypoxia promotes isocitrate dehydrogenase-dependent carboxylation of ?-ketoglutarate to citrate to support cell growth and viability, Proc. Natl. Acad. Sci. U S A., 108(49):19611-6 (2011).
Written Opinion for PCT/US2012/065731, 7 pages (dated Feb. 8, 2013).
Author Not Known, Definition of Chronic Hypoxia, Mosby's Dictionary of Medicine, Nursing, and Health Professions, 9th Edition (Print), p. 363 (2012).
Dang, L.et al., Cancer-associated IDH1 mutations produce 2-hydroxyglutarate, Nature, 462(7274):739-44 (2009).
Deberardinis, R.J. et al., Beyond aerobic glycolysis: transformed cells can engage in glutamine metabolism that exceeds the requirement for protein and nucleotide synthesis, Proc. Natl. Acad. Sci. USA, 104(49):19345-50 (2007).
Duan, J.X. et al., Potent and highly selective hypoxia-activated achiral phosphoramidate mustards as anticancer drugs, J. Med. Chem., 51(8):2412-20 (2008).
Extended European Search Report for EP 12850119.4, 13 pages (dated Sep. 2, 2015).
Kim, J.W. et al., HIF-1-mediated expression of pyruvate dehydrogenase kinase: a metabolic switch required for cellular adaptation to hypoxia, Cell Metab., 3(3):177-85 (2006).
Lum, J.J. et al., The transcription factor HIF-1alpha plays a critical role in the growth factor-dependent regulation of both aerobic and anaerobic glycolysis, Genes Dev., 21 (9):1037-49 (2007).
Papandreou, I. et al., HIF-1 mediates adaptation to hypoxia by actively downregulating mitochondrial oxygen consumption, Cell Metab., 3(3):187-97 (2006).

Patiar, S. and Harris, A.L., Role of hypoxia-inducible factor-1alpha as a cancer therapy target, Endocr. Relat. Cancer, 13 Suppl 1:S61-75 (2006).
Ward, P.S. et al., Identification of additional IDH mutations associated with oncometabolite R(-)-2-hydroxyglutarate production, Oncogene, 31(19):2491-8 (2012).
Ward, P.S. et al., The common feature of leukemia-associated IDH1 and IDH2 mutations is a neomorphic enzyme activity converting alpha-ketoglutarate to 2-hydroxyglutarate, Cancer Cell, 17(3):225-34 (2010).
Wise, D.R. et al., Myc regulates a transcriptional program that stimulates mitochondrial glutaminolysis and leads to glutamine addiction, Proc. Natl. Acad. Sci. USA, 105(48):18782-7 (2008).
Achouri, Y. et al., Identification of a dehydrogenase acting on D-2-hydroxyglutarate, The Biochemical Journal, 381: 35-42 (2004).
Albers, E., et al., Distribution of 14C-labelled carbon from glucose and glutamate during anaerobic growth of *Saccharomyces cerevisiae*, Microbiology, 14: 1683-1690 (1998).
Amary, M.F., et al., IDH1 and IDH2 mutations are frequent events in central chondrosarcoma and central and periosteal chondromas but not in other mesenchymal tumours, The Journal of Pathology, 224: 334-343 (2011).
Banks, J.L., et al., Integrated Modeling Program, Applied Chemical Theory (IMPACT), Journal of Computational Chemistry, 26(16):1752-1780 (2005).
Bensaad, K., and Harris, A.L., Hypoxia and metabolism in cancer, Advances in Experimental Medicine and Biology 772: 1-39 (2014).
Borger, D.R., et al., Frequent mutation of isocitrate dehydrogenase (IDH)1 and IDH2 in cholangiocarcinoma identified through broad-based tumor genotyping, The Oncologist 17, 72-79 (2012).
Cairns, R.A., et al., IDH2 mutations are frequent in angioimmunoblastic T-cell lymphoma, Blood, 119(8):1901-1903 (2012).
Chen, C., et al., Cancer-associated IDH2 mutants drive an acute myeloid leukemia that is susceptible to Brd4 inhibition, Genes & Development, 27:1974-1985 (2013).
Chowdhury, R., et al., The oncometabolite 2-hydroxyglutarate inhibits histone lysine demethylases, EMBO Reports, 12(5):463-469 (2011).
Figueroa, M.E., et al., Leukemic IDH1 and IDH2 mutations result in a hypermethylation phenotype, disrupt TET2 function, and impair hematopoietic differentiation, Cancer Cell, 18(6):553-567 (2010).
Friesner, R.A., et al., Extra precision glide: docking and scoring incorporating a model of hydrophobic enclosure for protein-ligand complexes, Journal of Medicinal Chemistry, 49(21):6177-6196 (2006).
Friesner, R.A., et al., Glide: a new approach for rapid, accurate docking and scoring. 1. Method and assessment of docking accuracy, Journal of Medicinal Chemistry, 47:1739-1749 (2004).
Gross, S., et al., Cancer-associated metabolite 2-hydroxyglutarate accumulates in acute myelogenous leukemia with isocitrate dehydrogenase 1 and 2 mutations, The Journal of Experimental Medicine, 207(2):339-344 (2010).
Halgren, T.A., et al., Glide: a new approach for rapid, accurate docking and scoring. 2. Enrichment factors in database screening, Journal of Medicinal Chemistry, 47:1750-1759 (2004).
Haliloglu, G., et al., L-2-hydroxyglutaric aciduria and brain tumors in children with mutations in the L2HGDH gene: neuroimaging findings, Neuropediatrics, 39:119-122 (2008).
Hu, C.J., et al., Differential roles of hypoxia-inducible factor 1alpha (HIF-1alpha) and HIF-2alpha in hypoxic gene regulation, Molecular and Cellular Biology, 23(24):9361-9374 (2003).
International Search Report for PCT/US2015/23038, 5 pages (dated Aug. 19, 2015).
Jacobson, M.P., et al., A hierarchical approach to all-atom protein loop prediction, Proteins: Structure, Function, and Bioinformatics, 55:351-367 (2004).
Jacobson, M.P., et al., On the role of the crystal environment in determining protein side-chain conformations, Journal of Molecular Biology, 320:597-608 (2002).
Kaelin, W.G., Jr., and McKnight, S.L., Influence of metabolism on epigenetics and disease, Cell, 153(1):56-69 (2013).

(56) References Cited

OTHER PUBLICATIONS

Kaelin, W.G., Jr., and Ratcliffe, P.J., Oxygen sensing by metazoans: the central role of the HIF hydroxylase pathway, Molecular Cell, 30:393-402 (2008).
Kats, L.M., et al., Proto-oncogenic role of mutant IDH2 in leukemia initiation and maintenance, Cell Stem Cell, 14(3):329-341 (2014).
Koivunen, P., et al., Transformation by the (R)-enantiomer of 2-hydroxyglutarate linked to EGLN activation, Nature, 483(7390):484-488 (2012).
Kooistra, S.M., and Helin, K., Molecular mechanisms and potential functions of histone demethylases, Nature Reviews Molecular Cell Biology, 13:297-311 (2012).
Kranendijk, M., et al., Progress in understanding 2-hydroxyglutaric acidurias, Journal of Inherited Metabolic Disease, 35:571-587 (2012).
Ley, T.J., et al., DNA sequencing of a cytogenetically normal acute myeloid leukemia genome, Nature, 456(7218):66-72 (2008).
Linster, C.L., et al., Metabolite damage and its repairer pre-emption, Nature Chemical Biology, 9:72-80 (2013).
Losman, J.A., and Kaelin, W.G., Jr., What a difference a hydroxyl makes: mutant IDH, (R)-2-hydroxyglutarate, and cancer, Genes & Development, 27:836-852 (2013).
Losman, J.A., et al., (R)-2-hydroxyglutarate is sufficient to promote leukemogenesis and its effects are reversible, Science, 339(6127):1621-1625 (2013).
Lu, C., et al., IDH mutation impairs histone demethylation and results in a block to cell differentiation, Nature, 483(7390):474-478 (2012).
Meister, A., Reduction of alpha gamma-diketo and alpha-keto acids catalyzed by muscle preparations and by crystalline lactic dehydrogenase, The Journal of Biological Chemistry, 184:117-129 (1950).
Metallo, C.M., et al., Reductive glutamine metabolism by IDH1 mediates lipogenesis under hypoxia, Nature, 481(7381):380-384 (2012).
Millard, P., et al., IsoCor: correcting MS data in isotope labeling experiments, Bioinformatics, 28(9):1294-1296 (2012).
Moroni, I., et al., L-2-hydroxyglutaric aciduria and brain malignant tumors: a predisposing condition?, Neurology, 62:1882-1884 (2004).
Nombela-Arrieta, C., et al., Quantitative imaging of haematopoietic stem and progenitor cell localization and hypoxic status in the bone marrow microenvironment, Nature Cell Biology, 15(5):533-543 (2013).
Olsson, M.H.M., et al., PROPKA3: Consistent Treatment of Internal and Surface Residues in Empirical pK(a) Predictions, J Chem Theory Comput, 7:525-537 (2011).
Ozer, A., and Bruick, R.K., Non-heme dioxygenases: cellular sensors and regulators jelly rolled into one?, Nature Chemical Biology, 3(3):144-153 (2007).
Parsons, D.W., et al., An integrated genomic analysis of human glioblastoma multiforme, Science, 321(5897):1807-1812 (2008).
Patel, J.P., et al., Prognostic relevance of integrated genetic profiling in acute myeloid leukemia, The New England Journal of Medicine, 366(12):1079-1089 (2012).
Patterson, A.L., et al., Absolute Configuration of Naturally Occurring Isocitric Acid, J Am Chem Soc, 84:309-310 (1962).
Rakheja, D. et al., Papillary thyroid carcinoma shows elevated levels of 2-hydroxyglutarate, Tumor Biology, 32:325-333 (2011).
Read, J.A., et al., Structural basis for altered activity of M- and H-isozyme forms of human lactate dehydrogenase, Proteins: Structure, Function, and Bioinformatics, 43:175-185 (2001).
Rohle, D., et al., An inhibitor of mutant IDH1 delays growth and promotes differentiation of glioma cells, Science, 340(6132):626-630 (2013).
Rzem, R., et al., A gene encoding a putative FAD-dependent L-2-hydroxyglutarate dehydrogenase is mutated in L-2-hydroxyglutaric aciduria, Proceedings of the National Academy of Sciences of the United States of America, 101(48):16849-16854 (2004).
Rzem, R., et al., L-2-hydroxyglutaric aciduria, a defect of metabolite repair, Journal of Inherited Metabolic Disease, 30:681-689 (2007).
Sasaki, M., et al., IDH1(R132H) mutation increases murine haematopoietic progenitors and alters epigenetics, Nature, 488(7413):656-659 (2012).
Schaap, F. et al., Mutations in the Isocitrate Dehydrogenase Genes IDH1 and IDH2 in Tumors, Adv Anat. Pathol., 20(1):32-38 (2013).
Schatz, L., and Segal, H.L., Reduction of alpha-ketoglutarate by homogeneous lactic dehydrogenase X of testicular tissue, The Journal of biological chemistry, 244(16):4393-4397 (1969).
Semenza, G.L., HIF-1 mediates metabolic responses to intratumoral hypoxia and oncogenic mutations, The Journal of Clinical Investigation, 123(9): 3664-3671 (2013).
Shim, E.H., et al., L-2-Hydroxyglutarate: An Epigenetic Modifier and Putative Oncometabolite in Renal Cancer, Cancer Discovery, 4(11):1290-1298 (2014).
Simon, M.C., and Keith, B., The role of oxygen availability in embryonic development and stem cell function, Nature Reviews Molecular Cell Biology, 9(4):285-296 (2008).
Sondergaard, C.R., et al., Improved Treatment of Ligands and Coupling Effects in Empirical Calculation and Rationalization of pK(a) Values, J Chem Theory Comput, 7:2284-2295 (2011).
Spencer, J.A., et al., Direct measurement of local oxygen concentration in the bone marrow of live animals, Nature, 508(7495):269-273 (2014).
Sprecher, M., et al., Stereochemical Course of the Isocitrate Lyase Reaction, The Journal of Biological Chemistry, 239(12):4268-4271 (1964).
Struys, E.A., et al., Mutations in the D-2-hydroxyglutarate dehydrogenase gene cause D-2-hydroxyglutaric aciduria, American Journal of Human Genetics, 76:358-360 (2005).
Struys, E.A., et al., Novel insights into L-2-hydroxyglutaric aciduria: mass isotopomer studies reveal 2-oxoglutaric acid as the metabolic precursor of L-2-hydroxyglutaric acid, Journal of Inherited Metabolic Disease, 30:690-693 (2007).
Suda, T., et al., Metabolic regulation of hematopoietic stem cells in the hypoxic niche, Cell Stem Cell, 9:298-310 (2011).
Tausendschon, M., et al., Hypoxia causes epigenetic gene regulation in macrophages by attenuating Jumonji histone demethylase activity, Cytokine, 53:256-262 (2011).
Terunuma, A., et al., MYC-driven accumulation of 2-hydroxyglutarate is associated with breast cancer prognosis, The Journal of Clinical Investigation, 124(1):398-412 (2014).
Vander Heiden, M.G., et al., Understanding the Warburg effect: the metabolic requirements of cell proliferation, Science, 324(5930):1029-1033 (2009).
Venneti, S., et al., Evaluation of histone 3 lysine 27 trimethylation (H3K27me3) and enhancer of Zest 2 (EZH2) in pediatric glial and glioneuronal tumors shows decreased H3K27me3 in H3F3A K27M mutant glioblastomas, Brain Pathol, 23(5):558-564 (2013).
Venneti, S., et al., Histone 3 lysine 9 trimethylation is differentially associated with isocitrate dehydrogenase mutations in oligodendrogliomas and high-grade astrocytomas, Journal of Neuropathology and Experimental Neurology, 72(4):298-306 (2013).
Wang, F., et al., Targeted inhibition of mutant IDH2 in leukemia cells induces cellular differentiation, Science, 340:622-626 (2013).
Wang, Y.H., et al., Cell-state-specific metabolic dependency in hematopoiesis and leukemogenesis, Cell, 158(6):1309-1323 (2014).
Ward, P.S., and Thompson, C.B., Metabolic reprogramming: a cancer hallmark even warburg did not anticipate, Cancer Cell, 21(3):297-308 (2012).
Wise, D.R., and Thompson, C.B., Glutamine addiction: a new therapeutic target in cancer, Trends in Biochemical Sciences, 35(8):427-433 (2010).
Written Opinion for PCT/US2015/23038, 7 pages (dated Aug. 19, 2015).
Xie, H., et al., Targeting lactate dehydrogenase—a inhibits tumorigenesis and tumor progression in mouse models of lung cancer and impacts tumor-initiating cells, Cell Metabolism, 19(5):795-809 (2014).
Xu, W., et al., Oncometabolite 2-hydroxyglutarate is a competitive inhibitor of alpha-ketoglutarate-dependent dioxygenases, Cancer Cell, 19(1):17-30 (2011).

(56) References Cited

OTHER PUBLICATIONS

Yan, H., et al., IDH1 and IDH2 mutations in gliomas, The New England Journal of Medicine, 360(8):765-773 (2009).
Zhdanov, A.V., et al., Differential contribution of certain metabolic substrates and cellular oxygen in HIF signalling, Experimental Cell Research, 330:13-28 (2014).
U.S. Appl. No. 14/358,962, filed May 16, 2014, Wise et al.
U.S. Appl. No. 15/129,167, filed Sep. 26, 2016, Intlekofer et al.
U.S. Appl. No. 16/452,297, filed Jun. 25, 2019, Intlekofer et al.
PCT/US2012/065731, May 30, 2014, International Preliminary Report on Patentability.
EP 15768552.0, Aug. 14, 2017, Partial Supplementary European Search Report.
EP 15768552.0, Nov. 14, 2017, Extended European Search Report.
PCT/US2015/023038, Jun. 25, 2015, Invitation to Pay Additional Fees.
PCT/US2015/023038, Oct. 13, 2016, International Preliminary Report on Patentability
International Preliminary Report on Patentability dated May 30, 2014 for International Application No. PCT/US2012/065731.
Partial Supplementary European Search Report dated Aug. 14, 2017 for European Application No. 15768552.0.
Extended European Search Report dated Nov. 14, 2017 for European Application No. 15768552.0.
Invitation to Pay Additional Fees dated Jun. 25, 2015 for International Application No. PCT/US2015/023038.
International Preliminary Report on Patentability dated Oct. 13, 2016 for International Application No. PCT/US2015/023038.

\* cited by examiner

A

B

C

2-HYDROXYGLUTARATE AS A BIOMARKER FOR CHRONIC HYPOXIA

CROSS-REFERENCE TO RELATED APPLICATIONS

This application is a U.S. national phase application under 35 U.S.C. § 371 of international PCT application No. PCT/US2012/065731, filed Nov. 18, 2012, which claims the benefit of and priority to U.S. provisional application Ser. No. 61/561,737, filed Nov. 18, 2011. The entire contents of these applications are hereby incorporated by reference.

This invention was made with government support under grant number CA105463 awarded by the National Institutes of Health. The government has certain rights in the invention.

BACKGROUND

A constant, uninterrupted supply of oxygen is essential to sustain life. Oxygen enters the body through the lungs and is transported to tissues via the blood, where it is utilized in cellular oxidative processes such as the citric acid cycle to provide energy for cells. A defect at any point in the system (i.e., heart, lungs, blood transportation, tissue delivery or cellular intake) can disrupt normal oxygenation and cause tissue damage, cell death, and/or death of the organism.

Hypoxia is a condition of low oxygen content in the blood or tissues resulting from an imbalance between oxygen supply and demand. Several different subtypes of hypoxia are known. For example, anemic hypoxia is due to a decreased concentration of functional hemoglobin or a reduced number of red blood cells. Hypoxic hypoxia results from a defective mechanism of oxygenation in the lungs, which may be caused by low tension of oxygen, abnormal pulmonary function, airway obstruction, or a right-to-left shunt in the heart. Oxygen affinity hypoxia is due to a reduced ability of hemoglobin to reduce oxygen. Tissue or cellular hypoxia is caused by interrupted coronary blood flow and/or a reduction in arterial blood oxygen partial pressure ($PO_2$).

Given the requirement of oxygen to sustain life, organisms have evolved diverse mechanisms to cope with both acute and chronic decreases in oxygen availability; i.e., with acute and chronic hypoxia. For multicellular organisms, particularly mammals, these mechanisms include erythropoiesis, angiogenesis and adaptive metabolic changes designed to maintain cellular activity at a minimum acceptable level. At the cellular level, a $PO_2$ of at least 18 mm Hg is necessary to sustain mitochondrial function, and to generate adenosine triphosphate ("ATP"), which is essential for all major cellular biochemical functions. Tissue or cellular hypoxia, therefore, may also be defined as a state where the rate of ATP synthesis becomes limited by the supply of oxygen.

As the name suggests, chronic hypoxia is marked by a chronic or consistent reduction in oxygen levels. For example, a non-severe form of chronic hypoxia may be observed in populations that dwell at high altitudes, where individuals are constantly exposed to lower $PO_2$ levels. Adaption to altitude is a well-recognized phenomenon. However, severe and consistent impairment of oxygen supply, pathophysiological chronic hypoxia, can exceed the adaptive mechanisms of both cells and tissues.

Acute hypoxia occurs in situations such as stroke, septic shock, myocardial infarction, and during surgical procedures. Chronic hypoxia, on the other hand, is associated with anemia, congestive heart failure, pulmonary disease, congenital heart disease, as well as cancer. For example, chronic hypoxia leads to increased pulmonary vasoconstriction in an attempt to redistribute pulmonary blood flow from regions of low $PO_2$ to high oxygen availability. However, chronic pulmonary vasoconstriction may result in pulmonary hypertension and increased load on the right ventricle, which may eventually lead to heart failure.

SUMMARY

Determining the presence of tissue hypoxia and distinguishing whether it is acute or chronic can be critical for prompt and proper diagnosis and treatment, but these determinations are often difficult in the clinical setting. For example, acute vs. chronic respiratory disorders are often assessed by the measurement of arterial blood gases and interpreted in the context of a patient history and the level of serum bicarbonate which reflects, given several underlying assumptions, how long the kidney has had to compensate. But if patient history is unreliable, the patient has underlying renal dysfunction, or if the patient has experienced vomiting, diarrhea, or drug toxicity, this approach is prone to substantial error. Furthermore, in the case of volume depletion or hypoperfusion of a particular tissue, the blood gas measurement obtained may be normal despite the presence of a localized tissue hypoxia.

The present invention provides, among other things, a novel biomarker for chronic hypoxia. According to the present invention, measurements of this biomarker, 2-hydroxyglutarate ("2HG"), can serve as a clinical modality that may be widely used in an emergency or intensive care setting to accurately and specifically identify patients with chronic tissue hypoxia. Measurement of 2HG in patient samples, and the relative presence or absence of 2HG therein, may also provide information that clinicians can correlate with a probable diagnosis of cancer, ischemia, organ failure, wound healing, tissue regeneration and repair, anemia, congestive heart failure, pulmonary disease, congenital heart disease, cardiovascular disease, as well as a negative diagnosis (e.g., normal or lack of a particular condition or disease).

As will be appreciated by those skilled in the art reading the present disclosure, the present invention defines individuals in whom the provided biomarker can or should be assayed and/or quantified, as well as technologies appropriate and/or useful for performing such assays and/or quantifications.

For example, in some embodiments the present invention provides a method of diagnosing chronic hypoxia in a subject, comprising measuring a level of at least one biomarker in a sample from the subject, wherein the at least one biomarker comprises 2-hydroxyglutarate, and determining whether the subject has chronic hypoxia based on the measured level of the at least one biomarker. In some embodiments, the method further comprises managing treatment of the subject based on the determination of chronic hypoxia. In some embodiments, the method further comprises measuring the at least one biomarker after subject management.

Some embodiments provide a method of measuring at least two biomarkers in a sample from a subject, wherein one of the at least two biomarkers is 2-hydroxyglutarate, and determining whether the subject has chronic hypoxia based on the measured level of the at least two biomarkers. In some embodiments, measuring the level of at least one biomarker comprises using mass spectrometry. In some embodiments, the measuring comprises using gas-chromatography-mass spectrometry, immune-based methods, or enzymatic assays. In certain embodiments, the determination of chronic hypoxia is based on the measured level of the at least one biomarker as compared to a control level. In some embodiments, the control level is indicative of the level of the one or more biomarkers in a control subject who does not have chronic hypoxia (i.e., is normoxic). In some embodiments, the control level is indicative of the level of the one or more biomarkers in a control subject who has acute hypoxia. In some embodiments, the control level is indicative of the level of the one or more biomarkers in a control population of subjects that does not have chronic hypoxia (i.e., normoxic controls). In other embodiments, the control level is indicative of the level of the one or more biomarkers in a control population of subjects that has acute hypoxia. In some embodiments, the difference between the levels of the one or more biomarkers measured in the sample and the control level correlates with the severity of chronic hypoxia in the subject.

In some embodiments of the invention, the at least one biomarker consists of 2-hydroxyglutarate. In certain embodiments, the sample is selected from a group comprising urine, blood, serum and cerebrospinal fluid. In certain embodiments, the sample comprises tumor cells or tissue cells adjacent to a tumor. In some embodiments, the at least one biomarker is selected from a group comprising, 2-hydroxyglutarate, α-ketoglutarate, IDH1, IDH2, HIF1, HIF2, or 2HG dehydrogenase. In certain embodiments, the sample is processed as described herein. Non-limiting, exemplary processing steps for use in embodiments of the invention include extraction of organic acids, column purification (e.g., anion exchange purification), chromatography (e.g., size-exclusion chromatography), centrifugation, and alcohol treatment (e.g. methanol or ethanol).

In certain embodiments, the present invention provides methods of generating a hypoxic profile in a subject, the methods comprising: obtaining a sample from the subject; using mass spectroscopy to measure the level of at least one first biomarker, wherein the at least one first biomarker comprises 2-hydroxyglutarate; measuring the level of at least one second biomarker; comparing the levels of the at least one first and second biomarkers to a reference profile comprised of levels of the same biomarkers obtained by identical methods from a population of control subjects; and based on the comparison, generating a hypoxic prolife that indicates whether the subject is normoxic or has chronic or acute hypoxia. In some embodiments, the reference profile is obtained from a population of healthy or normoxic control subjects. In other embodiments, the reference profile is obtained from a population of subjects having chronic hypoxia. In yet other embodiments, the reference profile is obtained from a population of subjects having acute hypoxia.

In certain embodiments, measuring the at least one second (e.g., α-ketoglutarate, IDH1, IDH2, HIF1, HIF2, or 2HG dehydrogenase) biomarker comprises measurement of protein expression level. In some embodiments, the protein expression level is measured by immunoassay using one or more antibodies that specifically bind to the at least one second biomarker. In another embodiment, measuring the at least one second biomarker comprises measurement of nucleic acid expression level. And in some embodiments, the nucleic acid expression level is measured by Northern blotting or RT-PCR amplification.

Embodiment of the invention further comprise methods of treating chronic hypoxia or an underlying cause thereof. These methods comprise measuring a level of 2-hydroxyglutarate in a sample from a subject; determining whether the level of 2-hydroxyglutarate is elevated at least two-fold compared to a normoxic control sample; and administering a treatment to the subject. Exemplary treatments for chronic hypoxia that may be applied in embodiments of the invention include supplemental oxygen therapy, transfusion of packed red blood cells, caffeine, vitamin therapy, antioxidant therapy, mechanical ventilation, positive pressure therapy, physical exercise, and surgical intervention. Exemplary treatments for the underlying cause of chronic hypoxia include treatments directed to chronic obstructive pulmonary disorder, airway obstruction, acute respiratory distress syndrome, pneumonia, pneumothorax, emphysema, congenital heart defects, pulmonary embolism, pulmonary edema, asthma, and cystic fibrosis.

Embodiments of the invention also comprise methods of screening a tumor sample for susceptibility to treatment with hypoxia-inducible prodrugs. Embodiments of the method comprise determining whether the level of 2-hydroxyglutarate is elevated at least two-fold compared to a control sample.

DEFINITIONS

"Biomarker": As defined herein, the term "biomarker" refers to a substance (e.g., 2HG) that can be used as an indicator of a disease, risk of developing the disease, carrier status, or responses to a therapeutic intervention. Typically, a suitable biomarker has a characteristic that can be objectively measured and evaluated as an indicator. In some embodiments, a biomarker is or comprises an organic biomolecule which is differentially present in a sample taken from a subject of one phenotypic status (e.g., having a disease; e.g. chronically hypoxic) as compared with another phenotypic status (e.g., not having the disease; e.g. normoxic or acutely hypoxic). A biomarker is differentially present between different phenotypic statuses if the difference in the mean or median expression and/or activity level (including absence of detectable expression and/or activity) of the biomarker in the different groups is calculated to be statistically significant. Common tests for statistical significance include, among others, t-test, ANOVA, Kruskal-Wallis, Wilcoxon, Mann-Whitney, odds ratio, Linear Discriminant Analysis, Quadratic Discriminant Analysis and K-nearest neighbor. Biomarkers, alone or in combination, provide measures of relative risk or likelihood that a subject belongs to one phenotypic status or another. Therefore, they are useful as markers for disease (diagnostics), therapeutic appropriateness or effectiveness of a drug, drug toxicity and indicators of proper treatment modalities.

"Detecting": As used herein, "detecting" refers to identifying the presence or absence of substance(s) (e.g., biomarkers) in a sample, quantifying the amount of substance(s) in the sample, qualifying the type of substance; and/or quantifying the activity level of substance(s) in the sample. Alternatively or additionally, "detecting" refers to identifying the presence, absence, and/or extent of chronic hypoxia in a subject, e.g., based upon the absence or presence (e.g., at a particular level or activity) of biomarkers of hypoxia, e.g., metabolites and/or metabolic byproducts (e.g., 2HG), in a sample obtained from a subject.

"Diagnosing the Status": As used herein, the terms "diagnosing", "diagnosing the status" or "determining the status", which may be used interchangeably, refer to the classification of a subject as (1) chronically hypoxic, (2) chronically hypoxic and not acutely hypoxic; (3) relatively likely (or unlikely) to suffer the onset of chronic hypoxia, and/or (4) at a particular point in the progression or response to treatment of chronic hypoxia. In particular embodiments, diagnosis is facilitated through analysis of an individual's hypoxic profile, as described below. In certain embodiments of the invention, diagnosis may be made without any overtly clinical manifestations of hypoxia, acute or otherwise. In other embodiments, a subject may manifest clinical symptoms of acute hypoxia but, through the methods disclosed herein, diagnosis of chronic hypoxia is confirmed. Thus, in some embodiments, "predicting the onset of chronic hypoxia" means classifying a patient as corresponding to a hypoxic profile derived from individuals who are confirmed to have chronic hypoxia. In some embodiments, "diagnosing the status" comprises an assessment of hypoxia within a tissue or solid tumor. In some embodiments, "diagnosing the status" comprises categorizing a subject as an appropriate or inappropriate candidate for a given treatment modality based on the status of hypoxia within the tissue or tumor. For example, diagnosing the status of a subject may comprise determining whether the subject is an appropriate candidate for hypoxia-inducible prodrugs.

"Differentially Produced": As used herein, the term "Differentially Produced", when used in connection with chronic hypoxia, refers to levels of 2HG production or synthesis, or quantities of 2HG, that are different in a subject (or a population of subjects) afflicted with chronic hypoxia relative to its levels or quantities in a healthy or normal subject (or a population of healthy or normal subjects) or a subject (or population of subjects) afflicted with acute hypoxia or other conditions associated with aberrant arterial or venous $PO_2$ levels. In some embodiments, the term encompasses levels of 2HG that are different for various sub-types of hypoxic (i.e., anemic hypoxia, hypoxic hypoxia, tissue hypoxia, oxygen affinity hypoxia). In some embodiments, the term encompasses 2HG levels that are different at different stages of chronic hypoxia (e.g., mild or early, severe or late). In some embodiments, differential production includes quantitative differences in 2HG levels; alternatively or additionally, in some embodiments, differential production refers to qualitative differences in 2HG levels. As described in greater detail below, differentially produced 2HG, alone or in combination with other differentially expressed biomarkers, is useful in a variety of different applications in diagnostic, staging, therapeutic, drug development and related areas. The levels of differentially produced 2HG disclosed herein can be described as a fingerprint or a signature of chronic hypoxia. Because, as described herein, 2HG is a biochemical metabolite that accumulates over time, elevated 2HG levels are preferentially indicative of prolonged states of hypoxia, i.e., chronic hypoxia, as compared hypoxic events of limited duration.

2HG levels can be used as a point of reference to compare and characterize unknown samples and samples for which further information is sought. For example, in some embodiments, a decreased level of 2HG production relative to a control (e.g., a sample taken from a subject at an earlier point in time or mean 2HG levels determined from a population of chronically hypoxic subjects) may indicate a positive treatment outcome. The term "decreased level of production", as used herein, refers to a decrease in production of at least 10% or more, for example, 20%, 30%, 40%, or 50%, 60%, 70%, 80%, 90% or more, or a decrease in expression of greater than 1-fold, 2-fold, 3-fold, 4-fold, 5-fold, 10-fold, 50-fold, 100-fold or more relative to a baseline as measured by one or more methods described herein. In some embodiments, however, an increased level of 2HG production can indicate chronic hypoxia and/or the presence or likelihood of a poor treatment outcome. The term "increased level of production", as used herein, refers to an increase in production of at least 10% or more, for example, 20%, 30%, 40%, or 50%, 60%, 70%, 80%, 90% or more or an increase in expression of greater than 1-fold, 2-fold, 3-fold, 4-fold, 5-fold, 10-fold, 50-fold, 100-fold or more relative to a baseline as measured by one or more methods, such as method described herein. In specific embodiments, tumor hypoxia is measured as a determinant of relapse-free survival and overall clinical outcome for cancer treatments comprising radiotherapy, surgery, chemotherapy and hypoxia-inducible prodrugs.

"Hypoxia" or "Hypoxic": As used herein, the terms "hypoxia" or hypoxic" refer to a decrease in tissue oxygen supply below normal levels. Also in some embodiments, the terms refer to a condition of low oxygen content in the blood. For adults, reference values of $PO_2$ in arterial and venous blood may be approximately about 80-100 mm Hg and 30-50 mm Hg, respectively. In particular embodiments, "hypoxia" or "hypoxic" conditions may be defined by arterial $PO_2$ values less than approximately 80 mm Hg and venous $PO_2$ values less than approximately 30 mm Hg. In some embodiments, "hypoxia" or "hypoxic" conditions may be defined by arterial $PO_2$ values less than approximately 60 mm Hg. In certain embodiments, "hypoxia" or "hypoxic" conditions may be defined by arterial $PO_2$ values less than approximately 50 mm Hg. In a particular embodiment, "hypoxia" or "hypoxic" conditions may be defined by arterial $PO_2$ values between approximately 50-20 mm Hg. Furthermore, "hypoxia" or "hypoxic" conditions may be differentiated from anoxia, which is defined as an absence or almost complete absence of oxygen from arterial blood or tissues. In some embodiments, type and severity of hypoxia may be defined by absolute or relative quantification or qualification of 2HG. "Hypoxia" or "Hypoxic" may also be defined by in vivo or in vitro atmospheric oxygen tension of approximately 0.5% $O_2$.

In some embodiments, "hypoxia" or "hypoxic" conditions may be defined by intra-tissue $PO_2$ levels less than about 10 mm Hg. In some embodiments, "hypoxia" or "hypoxic" conditions may be defined by intra-tissue $PO_2$ levels less than about 5 mm Hg. In some embodiments, "hypoxia" or "hypoxic" conditions may be defined by intra-tumor $PO_2$ levels less than about 10 mm Hg. In some embodiments, "hypoxia" or "hypoxic" conditions may be defined by intra-tumor $PO_2$ levels less than about 5 mm Hg.

"Hypoxia" or "hypoxic" conditions may be chronic or acute. "Chronic hypoxia", as used herein, may refer to sustained hypoxic conditions that result in a measurable increase in 2HG production. That is, chronic hypoxia may be defined as hypoxic conditions of sufficient duration to allow 2HG to accumulate above baseline levels. In some embodiments, chronic hypoxia is a hypoxic condition of more than 30 minutes, more than 1 hour, more than 2 hours, more than 3 hours, more than 4 hours, more than 5 hours, more than 10 hours, more than 12 hours, more than 24 hours, more than a day, or a week or more in duration. In some embodiments, chronic hypoxia is caused by consumption and depletion of oxygen by tissues or tumor cells between blood capillaries and the hypoxic regions. In contrast to the sustained conditions of chronic hypoxia, acute hypoxia is transient. In some embodiments, acute hypoxia occurs when there a temporary shutdown of vessels or microvasculature in tissues or tumors. In some embodiments, acute hypoxia occurs as a result of fluctuations in red blood cell levels.

"Mass spectrometer": "Mass spectrometer" refers to a gas phase ion spectrometer that measures a parameter that can be translated into mass-to-charge ratios of gas phase ions. Mass spectrometers generally include an ion source and a mass analyzer. Examples of mass spectrometers are time-of-flight, magnetic sector, quadrupole filter, ion trap, ion cyclotron resonance, electrostatic sector analyzer and hybrids of these. "Mass spectrometry" refers to the use of a mass spectrometer to detect gas phase ions.

"Metabolite": As used herein, "metabolite" refers to any substance produced or used during a physical or chemical processes within the body that creates and/or uses energy, such as: digesting food and nutrients, eliminating waste through urine and feces, breathing, circulating blood, and regulating temperature. The term "metabolic precursors" refers to compounds from which the metabolites are made. The term "metabolic products" refers to any substance that is part of a metabolic pathway (e.g., metabolite, metabolic precursor).

"Normoxic": As used herein, the term "normoxic" refers to serum or tissue $PO_2$ levels that are not chronically or acutely hypoxic. When used to modify the term "individual" or "subject", the term refers to an individual or group of individuals who does not have a chronic or acute hypoxia. For example, in particular embodiments, normoxic individuals have an arterial $PO_2$ of between approximately 80-100 mm Hg and/or a venous $PO_2$ of approximately 30-50 mm Hg. "Normoxia" or "Normoxic" may also be defined by in vivo or in vitro atmospheric oxygen tension of approximately 21% $O_2$. In some embodiments, normoxic levels are established by consideration of levels present across or within a population of individuals who do not have a chronic or acute hypoxia. For example, in some embodiments, normoxic levels represent an average, median, or mean value of levels across or within such a population, typically showing statistical significance.

In some embodiments, "normoxic" conditions may be defined by intra-tissue $PO_2$ levels greater than about 10 mm Hg. In some embodiments, "normoxic" conditions may be defined by intra-tissue $PO_2$ levels greater than about 5 mm Hg.

"Partial Pressure": As used herein, the term "partial pressure" refers to the fact that in a mixture of gases, the total gas pressure is equal to the sum of the partial pressures of each gas. In particular embodiments of the invention, blood gas analysis may be performed to determine the partial pressures of oxygen and carbon dioxide, referred to as $PO_2$ and $PCO_2$, respectively. The units of $PO_2$ or $PCO_2$ may be represented in millimeters of mercury ("mm Hg"), or torr, and alternatively in the international unit of pascals ("Pa") (1 mm Hg=133.3224 Pa). At 37° C. and normally encountered atmospheric pressure, the total pressure, P, is equal to the sum of partial pressures ($PO_2$, $PCO_2$, $PN_2$ and $PH_2O$). However, extreme examples of lower air pressure (hypobarism) and higher air pressure (hyperbarism) may be encountered in particular embodiments of the invention. Thus, embodiments of the present invention encompass corrections of blood gas data for changes in total atmospheric pressure. In some embodiments, $PO_2$ levels may be measured by an Eppendorf $PO_2$ microelectrode system.

"Sample": As used herein, the term "sample" encompasses any sample obtained or derived through processing (i.e., through intervention) from a primary biological source. The terms "biological sample" and "sample" are used interchangeably. A biological sample can, by way of non-limiting example, include cerebrospinal fluid (CSF), blood, amniotic fluid, sera, urine, feces, epidermal sample, skin sample, cheek swab, sperm, amniotic fluid, cultured cells, bone marrow sample and/or chorionic villi. As used herein, "serum" refers to the fluid portion of the blood obtained after removal of the fibrin clot and blood cells, distinguished from the plasma in circulating blood. As used herein, "plasma" refers to the fluid, noncellular portion of the blood, distinguished from the serum obtained after coagulation. A biological sample can also be, e.g., a sample obtained from any organ or tissue (including a biopsy or autopsy specimen), can comprise cells (whether primary cells or cultured cells), medium conditioned by any cell, tissue or organ, tissue culture. In some embodiments, biological samples suitable for the invention are samples which have been processed to release or otherwise make available a nucleic acid for detection as described herein. Fixed or frozen tissues also may be used.

"Subject": As used herein, the term "subject" refers to a human or any non-human animal (e.g., mouse, rat, rabbit, dog, cat, cattle, swine, sheep, horse or primate). A human includes pre- and postnatal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

"Treat," "treating" and "treatment": As used herein, the terms "treat," "treating" and "treatment," contemplate an action that occurs while a patient is suffering from or susceptible to the specified disease or disorder, which reduces the incidence and/or severity of, and/or delays onset of, one or more symptoms or manifestations of the disease or disorder. Thus, "treat", "treating", and "treatment" refer to any type of treatment that imparts a benefit to a subject afflicted with a disease, including improvement in the condition of the subject (e.g., in one or more symptoms), delay in the progression of the disease, prevention or delay of the onset of the disease, etc.

DESCRIPTION OF THE DRAWING

In FIG. 1(A), SF188 cells were plated in complete medium equilibrated with 21% $O_2$ (Normoxia) or 0.5% $O_2$ (Hypoxia), total viable cells were counted 24 h and 48 h later (Day 1 and Day 2), and population doublings were calculated. Data are the mean+/−SEM of 4 independent experiments. FIG. 1(B) show a western blot demonstrating stabilized HIF1α protein in cells cultured in hypoxia compared with normoxia. In FIG. 1(C), cells were grown in normoxia or hypoxia for 24 h, following which culture medium was collected. Medium glucose and lactate levels were measured and compared with the levels in fresh medium. In FIG. 1(D), cells were cultured for 24 h as in (C). Intracellular metabolism was then quenched with 80% MeOH pre-chilled to −80° C. that was spiked with a $^{13}$C-labeled citrate as an internal standard. Metabolites were then extracted, and intracellular citrate levels were analyzed with GC-MS and normalized to cell number. Data for (C) and (D) are the mean+/−SEM of 3 independent experiments. FIG. 1(E) shows a model depicting the pathway for cit+2 production from [U-$^{13}$C]glucose. Glucose uniformly $^{13}$C-labeled will generate pyruvate+3. Pyruvate+3 can be oxidatively decarboxylated by PDH to produce acetyl-CoA+2, which can condense with unlabeled oxaloacetate to produce cit+2. In FIG. 1(F), cells were cultured for 24 h as in (C) and (D), followed by an additional 4 h of culture in glucose-deficient medium supplemented with 10 mM [U-$^{13}$C]glucose. Intracellular metabolites were then extracted, and $^{13}$C-enrichment in cellular citrate was analyzed by GC-MS and normalized to the total citrate pool size. Data are the mean+/−SD of 3 independent cultures from a representative of 2 independent experiments. *P<0.05, ***P<0.001.

In FIG. 2(A), SF188 cells were cultured for 24 h in complete medium equilibrated with either 21% $O_2$ (Normoxia) or 0.5% $O_2$ (Hypoxia). Culture medium was then removed from cells and analyzed for glutamine levels which were compared to the glutamine levels in fresh medium. Data are the mean±SEM of 3 independent experiments. FIG. 2(B), shows that the requirement for glutamine to maintain hypoxic cell viability can be satisfied by α-ketoglutarate. Cells were cultured in complete medium equilibrated with 0.5% $O_2$ for 24 h, followed by an additional 48 h at 0.5% $O_2$ in either complete medium (+Gln), glutamine-deficient medium (−Gln), or glutamine-deficient medium supplemented with 7 mM dimethyl α-ketoglutarate (−Gln+αKG). All medium was pre-conditioned in 0.5% $O_2$. Cell viability was determined by trypan blue dye exclusion. Data are the mean and range from 2 independent experiments. FIG. 2(C) depicts a model of the pathways for cit+4 and cit+5 production from [U-$^{13}$C]glutamine (glutamine+5). Glutamine+5 is catabolized to α-ketoglutarate+5, which can then contribute to citrate production by two divergent pathways. Oxidative metabolism produces oxaloacetate+4, which can condense with unlabeled acetyl-CoA to produce cit+4. Alternatively, reductive carboxylation produces isocitrate+5, which can isomerize to cit+5. FIG. 2(D) shows that glutamine contributes to citrate production through increased reductive carboxylation relative to oxidative metabolism in hypoxic proliferating cancer cells. Cells were cultured for 24 h as in (A), followed by 4 h of culture in glutamine-deficient medium supplemented with 4 mM [U-$^{13}$C]glutamine. $^{13}$C enrichment in cellular citrate was quantitated with GC-MS. Data are the mean+/−SD of 3 independent cultures from a representative of 3 independent experiments. **P<0.01.

In FIG. 3(A), SF188 cells were cultured in complete medium equilibrated with either 21% $O_2$ (Normoxia) or 0.5% $O_2$ (Hypoxia) for 24 h. Intracellular metabolism was then quenched with 80% MeOH pre-chilled to −80° C. that was spiked with a $^{13}$C-labeled citrate as an internal standard. Metabolites were extracted, and intracellular aspartate (asp), malate (mal), and fumarate (fum) levels were analyzed with GC-MS. Data are the mean±SEM of 3 independent experiments. FIG. 3(B) depicts a model for the generation of aspartate, malate, and fumarate isotopomers from [U-$^{13}$C]glutamine (glutamine+5). Glutamine+5 is catabolized to j-ketoglutarate+5. Oxidative metabolism of α-ketoglutarate+5 produces fumarate+4, malate+4, and oxaloacetate(OAA)+4 (OAA+4 is in equilibrium with aspartate+4 via transamination). Alternatively, α-ketoglutarate+5 can be reductively carboxylated to generate isocitrate+5 and citrate+5. Cleavage of citrate+5 in the cytosol by ATP-citrate lyase (ACL) will produce oxaloacetate+3 (in equilibrium with aspartate+3). Oxaloacetate+3 can be metabolized to malate+3 and fumarate+3. In FIG. 3(C), SF188 cells were cultured for 24 h as in 3(A), and then cultured for an additional 4 h in glutamine-deficient medium supplemented with 4 mM [U-$^{13}$C]glutamine. $^{13}$C enrichment in cellular aspartate, malate, and fumarate was determined by GC-MS and normalized to the relevant metabolite total pool size. Data shown are the mean+/−SD of 3 independent cultures from a representative of 3 independent experiments. P<0.01, *P<0.001.

FIG. 4(A) shows that α-ketoglutarate and 2HG increase in hypoxia. SF188 cells were cultured in complete medium equilibrated with either 21% $O_2$ (Normoxia) or 0.5% $O_2$ (Hypoxia) for 24 h. Intracellular metabolites were then extracted, cell extracts spiked with a $^{13}$C-labeled citrate as an internal standard, and intracellular α-ketoglutarate and 2HG levels were analyzed with GC-MS. Data shown are the mean±SEM of 3 independent experiments. FIG. 4(B) depicts a model for reductive metabolism from glutamine-derived α-ketoglutarate. Glutamine+5 is catabolized to α-ketoglutarate+5. Carboxylation of α-ketoglutarate+5 followed by reduction of the carboxylated intermediate (reductive carboxylation) produces isocitrate+5, which can then isomerize to cit+5. In contrast, reductive activity on α-ketoglutarate+5 that is uncoupled from carboxylation will produce 2HG+5. FIG. 4(C) shows that IDH2 is required for reductive metabolism of glutamine-derived α-ketoglutarate in hypoxia. SF188 cells transfected with an siRNA against IDH2 (siIDH2) or non-targeting negative control (siCTRL) were cultured for 2 days in complete medium equilibrated with 0.5% $O_2$. (Top) Cells were then cultured at 0.5% $O_2$ for an additional 4 h in glutamine-deficient medium supplemented with 4 mM [U-$^{13}$C]glutamine. $^{13}$C enrichment in intracellular citrate and 2HG was determined and normalized to the relevant metabolite total pool size. (Bottom) Cells transfected and cultured in parallel at 0.5% $O_2$ were counted by hemacytometer (excluding non-viable cells with trypan blue staining) or harvested for protein to assess IDH2 expression by Western blot. Data shown for GC-MS and cell counts are the mean+/−SD of 3 independent cultures from a representative experiment. **P<0.01, P<0.001.

FIG. 5(A) depicts a model of how HIF1 signaling's inhibition of pyruvate dehydrogenase (PDH) activity and promotion of lactate dehydrogenase-A (LDH-A) activity can block the generation of mitochondrial acetyl-CoA from glucose-derived pyruvate, thereby favoring citrate synthesis from reductive carboxylation of glutamine-derived α-ketoglutarate. FIG. 5(B) shows a western blot demonstrating HIF1α protein in RCC4 VHL$^{-/-}$ cells in normoxia with a non-targeting shRNA (shCTRL), and the decrease in HIF1 α protein in RCC4 VHL$^{-/-}$ cells stably expressing HIF1α shRNA (shHIF1α). FIG. 5(C) shows that HIF1-induced reprogramming of glutamine metabolism. Cells from 5(B) at 21% $O_2$ were cultured for 4 h in glutamine-deficient medium supplemented with 4 mM [U-$^{13}$C]glutamine. Intracellular metabolites were then extracted, and $^{13}$C enrichment in cellular citrate was determined by GC-MS. Data shown are the mean+/−SD of 3 independent cultures from a representative of 3 independent experiments. ***P<0.001.

DETAILED DESCRIPTION OF CERTAIN EMBODIMENTS

Figure 1:
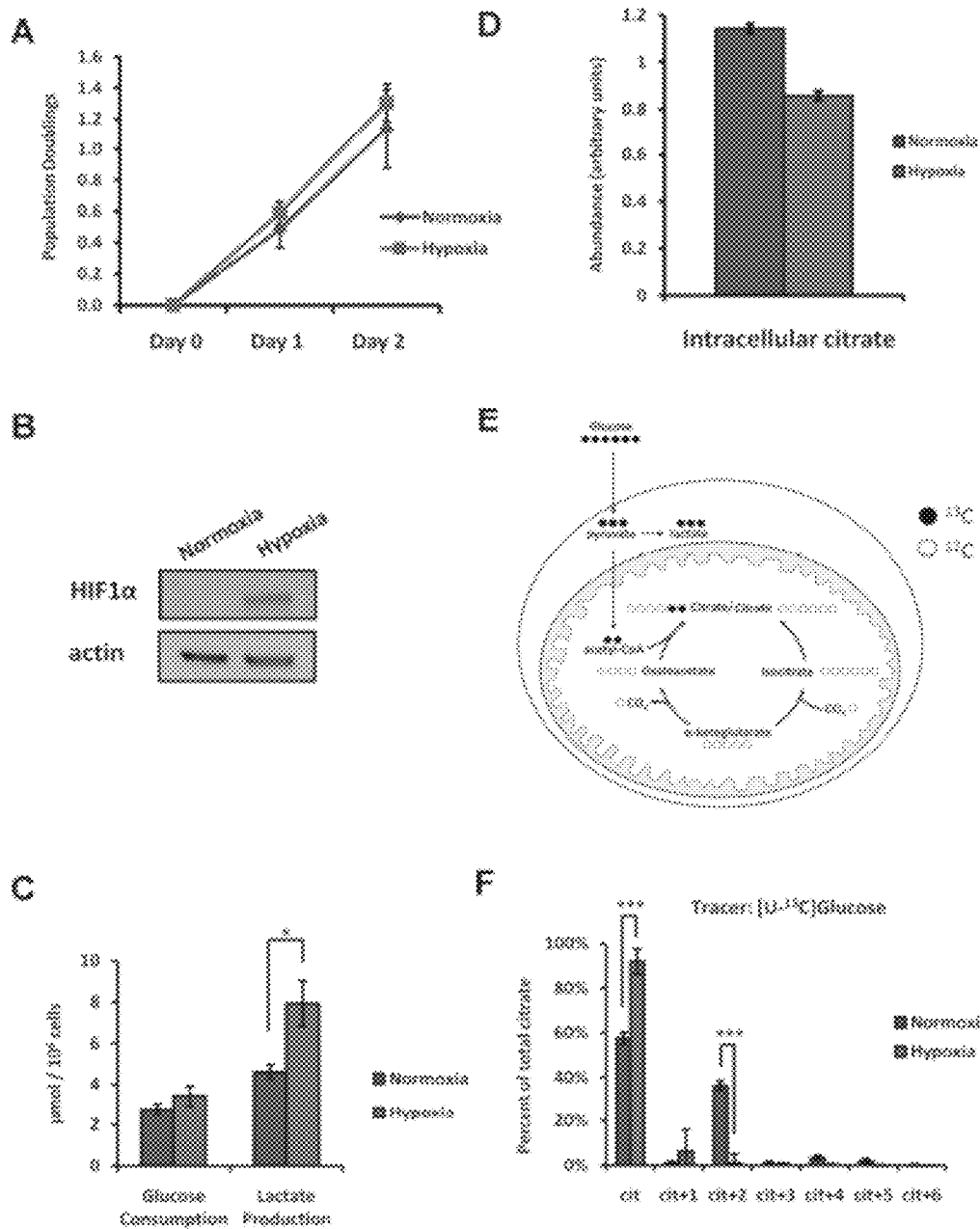
FIG. 1 shows that SF188 glioblastoma cells proliferate at 0.5% O2 despite a profound reduction in glucose-dependent citrate synthesis.

The citric acid or tricarboxylic acid ("TCA") cycle is well known for its role in catabolism and energy generation. It addition, it is an important source of biosynthetic intermediates via a number of anabolic pathways. These pathways draw carbon from the cycle by utilizing intermediates in the cycle. For example, citrate is the central biosynthetic precursor for fatty acid and sterol synthesis. Under normal conditions, citrate is generated via the TCA cycle from glucose-derived pyruvate and acetyl-CoA. The breakdown of citrate by ATP-citrate lyase is a primary source of acetyl-CoA for protein acetylation. Metabolism of cytosolic citrate by aconitase and isocitrate dehydrogenase 1 (IDH1) can also provide the cell with a source of NADPH for redox regulation and anabolic synthesis.

Citrate plays a critical role at the center of cancer cell metabolism, where the rapidly dividing cells increase the demand for fatty acid and cholesterol synthesis. Mammalian cells depend on the catabolism of glucose and glutamine to fuel proliferation. In cancer cells cultured at atmospheric oxygen tension (21% $O_2$), glucose and glutamine have been shown to both contribute to the cellular citrate pool, with glutamine providing the major source of the 4 carbon molecule oxaloacetate and glucose providing the major source of the 2 carbon molecule acetyl-CoA. The condensation of oxaloacetate and acetyl-CoA via citrate synthase generates the 6 carbon citrate molecule. However, both the conversion of glucose-derived pyruvate to acetyl-CoA by pyruvate dehydrogenase (PDH) and the conversion of glutamine to oxaloacetate through the TCA cycle depend on NAD+, which can be compromised under hypoxic conditions. Moreover, proliferating cells that exhibit aerobic glycolysis and those exposed to hypoxia predominately convert glucose to lactate, directing glucose carbon away from the TCA cycle. This raises the question of how proliferating cells in hypoxia continue to synthesize the citrate required for macromolecular synthesis.

Cancer cells are an appropriate model to answer this question as many cancers and stem/progenitor cells can continue proliferating in the setting of limited oxygen availability. Louis Pasteur first highlighted the impact of hypoxia on nutrient metabolism based on his observation that hypoxic yeast cells preferred to convert glucose into lactic acid rather than burning it in an oxidative fashion. The molecular basis for this shift in mammalian cells has been linked to activity of the transcription factor HIF1. HIF1 is regulated at the level of its labile HIF1α subunit by prolyl hydroxylation, a post-translational modification which targets HIF1α for ubiquitination by the von Hippel-Lindau (VHL) E3 ubiqutin ligase and subsequent proteasomal degradation. In hypoxia, prolyl hydroxylase activity is limited by lack of oxygen, leading to the stabilization of the HIF1α subunit. HIF1α stabilization can also occur in normoxia through several mechanisms, including through loss of the VHL tumor suppressor, a common occurrence in clear cell renal carcinoma. Although hypoxia and/or HIF1α stabilization is a common feature of multiple cancers, to date the source of citrate in the setting of hypoxia or HIF activation has not been determined in either normal or cancerous cells.

As shown in the examples below, embodiments of the present invention encompass the study of the sources of hypoxic citrate synthesis in a glioblastoma cell line that proliferates in chronic hypoxia. Glucose uptake and conversion to lactic acid increased in hypoxia. However, glucose conversion into citrate dramatically declined. Glutamine consumption remained constant in chronic hypoxia and the hypoxic cells were dependent upon the use of glutamine in hypoxia as a source of α-ketoglutarate. Glutamine provided the major carbon source for citrate synthesis during hypoxia. However, the TCA cycle-dependent conversion of glutamine into citric acid was significantly suppressed. In contrast, there was a relative increase in glutamine-dependent citrate production in hypoxia that resulted from carboxylation of α-ketoglutarate. This reductive synthesis required the presence of mitochondrial isocitrate dehydrogenase 2 (IDH2). In confirmation of the reverse flux through IDH2, the increased reductive metabolism of glutamine-derived α-ketoglutarate in chronic hypoxia was associated with increased synthesis of the metabolite 2HG. Finally, constitutive HIF1α-expressing cells also demonstrated significant reductive carboxylation dependent synthesis of citrate and a relative defect in the oxidative conversion of glutamine into citrate. Collectively, the present disclosure shows that mitochondrial glutamine metabolism can be rerouted through IDH2-dependent citrate synthesis in support of cell growth during chronic hypoxia and, consequently, that this phenomenon can be detected and quantitated through increased synthesis or production of 2HG.

Biomarkers for Chronic Hypoxia

The present invention, among other things, provides a novel biomarker for chronic hypoxia. It has been determined in accordance with the present invention that 2HG, a rare metabolite found at trace amounts in mammalian cells and body fluids under normal conditions, is reproducibly elevated at least three-fold under chronic conditions of inadequate oxygen supply and is sufficient to serve as a biomarker for chronic hypoxia. 2HG arises from the non-carboxylating reduction of the citric acid cycle intermediate α-ketoglutarate in the mitochondria. Under normal conditions, the extent of this reaction to produce 2HG is minimal, and the 2HG that is produced does not substantially accumulate due to the enzymatic activity of 2HG dehydrogenase, which functions to oxidize 2HG back to α-ketoglutarate. However, as disclosed herein, after 2 days of chronic exposure to low oxygen, the normal oxidative metabolism of α-ketoglutarate through the citric acid cycle is suppressed in human cells and α-ketoglutarate preferentially undergoes reductive metabolism that leads to the accumulation of 2HG. Furthermore, the present disclosure demonstrates that the reductive reaction to produce 2HG is dependent on reverse flux through mitochondrial NADP+-isocitrate dehydrogenase 2 (IDH2). The accumulation of 2HG observed after 2 days of hypoxia is consistent with the oxidative activity of the 2HG dehydrogenase being impaired under these conditions.

2HG elevation occurs with chronic hypoxia and reflects alterations in metabolism at the cellular and subcellular (i.e. mitochondrial) level. Known situations independent of hypoxia where serum 2HG is elevated are limited to rare inborn errors of metabolism involving germline genetic mutations, or myeloid hematologic malignancies with specific somatic mutations in the IDH1/2 genes. These patients are rare relative to the number presenting with cardiopulmonary disease and/or tissue hypoxia, and their symptoms are distinctive and non-overlapping. Therefore, the risks of false positives with a 2HG serum test for chronic hypoxia are likely to be low. In contrast, currently used methods for distinguishing acute vs. chronic hypoxia in the blood, such as the interpretation of serum bicarbonate or hemoglobin/hematocrit values, are liable to both false positive and false negative results, as they rest on several assumptions concerning proper adaptive responses by the kidneys and bone marrow, respectively.

Specifically, to date 2HG has only been shown to be elevated in human tissues and body fluids due to the specific genetic events of either neomorphic gain-of-function mutations in the IDH1/2 genes (facilitating overproduction of 2HG) or loss-of-function mutations mutations in the 2HG dehydrogenase gene (leading to an inability to effectively metabolize and remove 2HG). The embodiment of the inventions disclosed herein are the first and only known description of 2HG accumulation that is independent of these genetic alterations and that occurs due to the altered activity of normal, non-mutated, metabolic enzymes.

Typically, a suitable biomarker has a characteristic that can be objectively measured and evaluated as an indicator. In embodiments of the present invention, the quantity of intercellular 2HG production or the amounts or levels of 2HG in a biological sample are objectively measured and evaluated as an indicator of chronic hypoxia. 2HG is differentially produced between subjects suffering from chronic hypoxia and normal healthy or normoxic individuals. (see, e.g., FIG. 4A.) 2HG may also be differentially produced between subjects suffering from chronic hypoxia and acute hypoxia. Thus, in some embodiments, "differential production" may be used to generate a hypoxic profile that indicates the oxygenation status of an individual or subject. As used herein, the term "hypoxic profile" refers to methods of comparing 2HG levels or patterns in two or more samples (e.g., samples obtained from subjects known or suspected to be suffering from chronic hypoxia, or subjects of indeterminate hypoxic status, vs. (1) control samples obtained from healthy control individuals (or derived—e.g. mean or median measurements—from a population of healthy individuals) or (2) control samples obtained from individuals (or derived—e.g. mean or median measurements—from a population of individuals) suffering from acute hypoxia. Typically, 2HG is differentially produced if the difference (e.g., increase or decrease) in 2HG levels is statistically significant (i.e., the difference is not caused by random variations). In some embodiments, 2HG is differentially produced if the difference between two samples is more than 20%, 30%, 40%, 50%, 60%, 70%, 80%, 90%, 1-fold, 1.2-fold, 1.5-fold, 1.75-fold, 2-fold, 2.25-fold, 2.5-fold, 2.75-fold, or 3-fold.

As discussed in the Examples section, 2HG has been discovered to be a biomarker of chronic hypoxia. The present invention provides the particular insight that 2HG levels can be reliably and rapidly measured as a clinical biomarker of chronic hypoxia by approaches such as mass spectrometry (including gas chromatography-mass spectrometry (GC-MS)), enzymatic and immune-based methods. 2HG has been shown to accumulate extracellularly when it is overproduced in cells, demonstrating its cell permeability. (Ward, P. S. et al. "The common feature of leukemia-associated IDH1 and IDH2 mutations is a neomorphic enzyme activity converting α-ketoglutarate to 2-hydroxyglutarate", *Cancer Cell*, 17:225-234 (2010), incorporated by reference herein). Moreover, in rare clinical pediatric patients with a genetic deficiency in the 2HG-dehydrogenase, 2HG can be reliably measured and found to be elevated in patient sera and other body fluids. (See Capper, D. et al. "2-Hydroxyglutarate concentration in serum from patients with gliomas does not correlate with IDH1/2 mutation status or tumor size", *Int. J. Cancer* (2011)). Thus, a 2HG elevation from patient plasma or serum can serve as a biomarker for adult patients with chronic hypoxia that can be measured non-invasively.

2HG levels may be measured alone or in combination, for example, as an indicator of chronic hypoxia, to monitor progression or abatement of hypoxia, and/or to monitor treatment response or optimization. In some embodiments, at least two, three, four, five, six, seven, eight, nine, ten or more biomarkers may be measured in combination with 2HG as a hypoxic profile panel. Exemplary additional hypoxic biomarkers may include the use or assessment of expression or activity levels of: 2-nitroimidazole and derivatives thereof, aconitase, α-ketoglutarate dehydrogenase, carbonic anhydrase, clusterin, phosphorylation status of cAMP response element binding protein, creatine kinase isoenzyme (CK-BB), neuron-specific enolase (NSE), differentiated embryo-chondrocyte expressed gene 1 ("DEC1"), epidermal growth factor receptor, erythropoietin, fibrotic focus, fluoromisonidazole, glucose transporters 1 and 3, hypoxia-inducible factors 1 and 2 ("HIF1 and HIF2"), hypoxia-inducible protein 2, isocitrate dehydrogenase 2 ("IDH2"), isocitrate dehydrogenase 2 ("IDH1"), iodovinylmisonidazole, lactate, $PCO_2$, pimonidazole, pyruvate dehydrogenase, S100, succinate, tronponin T, VEGF, and 2HG dehydrogenase.

2HG levels may be detected by any method known to those of skill in the art. Non-limiting examples of various detection methodologies are discussed below. The present invention provides the particular insight that methodologies such as gas chromatography-mass spectrometry ("GC-MS"), liquid chromatography-mass spectrometry ("LC-MS"), enzymatic assays and immune-based methods may be used to measure 2HG levels in a clinical setting as a biomarker of chronic hypoxia. In embodiments where additional biomarkers are measured, the additional markers may be measured by any method known to those of skill in the art; for example, immunoassays (e.g., Western blotting), hybridization (e.g. Northern blotting), RT-PCR, and mass spectrometry). For example, in a particular embodiment, serum 2HG levels may be assayed by GC-MS and evaluated or correlated in combination with nucleic acid- or immunoassay-based measures of IDH1/2, HIF1/2, or 2HG dehydrogenase.

Biological Samples

Embodiments of the invention may be applied to any type of biological samples allowing 2HG and optionally additional biomarkers to be assayed. Examples of suitable biological samples include, but are not limited to, blood, serum, tissue, tumor, cerebrospinal fluid (CSF), cells, tissue, mouthwash, plasma, urine, stool, saliva, cord blood, chorionic villus sample, chorionic villus sample culture, amniotic fluid, amniotic fluid culture, transcervical lavage fluid. Biological samples suitable for use in accordance with the invention may be fresh or frozen samples collected from a subject, or archival samples with known diagnosis, treatment and/or outcome history. Biological samples may be collected by any invasive or non-invasive means, such as, for example, by drawing blood from a subject, or using fine needle aspiration or needle biopsy, or by surgical biopsy.

In certain embodiments, biological samples may be used without or with limited processing of the sample. In some embodiments, the samples are processed for GC-MS and LC-MS as described below. In some embodiments requiring detection and/or measurement of one or more proteins or polynucleotides in the sample, protein extract may be prepared from a biological sample. In some embodiments, a protein extract contains substantially the total protein content. In some embodiments, protein extracts containing one or more of membrane proteins, nuclear proteins, and cytosolic proteins may be prepared. Methods of protein extraction are well known in the art (see, for example "Protein Methods", D. M. Bollag et al., 2nd Ed., 1996, Wiley-Liss; "Protein Purification Methods: A Practical Approach", E. L. Harris and S. Angal (Eds.), 1989; "Protein Purification Techniques: A Practical Approach", S. Roe, 2nd Ed., 2001, Oxford University Press; "Principles and Reactions of Protein Extraction, Purification, and Characterization", H. Ahmed, 2005, CRC Press: Boca Raton, Fla.). Numerous different and versatile kits can be used to extract proteins from bodily fluids and tissues, and are commercially available from, for example, BioRad Laboratories (Hercules, Calif.), BD Biosciences Clontech (Mountain View, Calif.), Chemicon International, Inc. (Temecula, Calif.), Calbiochem (San Diego, Calif.), Pierce Biotechnology (Rockford, Ill.), and Invitrogen Corp. (Carlsbad, Calif.). User Guides that describe in great detail the protocol to be followed are usually included in all these kits. Sensitivity, processing time and costs may be different from one kit to another. One of ordinary skill in the art can easily select the kit(s) most appropriate for a particular situation. After the protein extract has been obtained, the protein concentration of the extract is preferably standardized to a value being the same as that of the control sample in order to allow signals of the protein markers to be quantitated. Such standardization can be made using photometric or spectrometric methods or gel electrophoresis.

DNA or RNA can be isolated from the sample according to any of a number of methods well known to those of skill in the art. Methods of DNA and RNA extraction are well known in the art (see, for example, J. Sambrook et al., "Molecular Cloning: A Laboratory Manual", 1989, $2^{nd}$ Ed., Cold Spring Harbor Laboratory Press: Cold Spring Harbor, N.Y.). In one embodiment, total RNA is isolated using the TRIZOL reagent (Life Technologies, Gaithersburg Md.), and mRNA is isolated using oligo d(T) column chromatography or glass beads. Alternatively, when biomarker polynucleotides are derived from an mRNA, the biomarker polynucleotides can be a cDNA reverse-transcribed from an mRNA, an RNA transcribed from that cDNA, a DNA amplified from that cDNA, an RNA transcribed from the amplified DNA, and the like. When the biomarker polynucleotide is derived from DNA, the biomarker polynucleotide can be DNA amplified from DNA or RNA reverse transcribed from DNA.

When biomarker polynucleotides are amplified, it is desirable to amplify the nucleic acid sample and maintain the relative abundances of the original sample, including low abundance transcripts. Total mRNA can be amplified by reverse transcription using a reverse transcriptase and a primer consisting of oligo d(T) and a sequence encoding the phage T7 promoter to provide a single-stranded DNA template. The second DNA strand is polymerized using a DNA polymerase and a RNAse which assists in breaking up the DNA/RNA hybrid. After synthesis of the double-stranded DNA, T7 RNA polymerase can be added, and RNA transcribed from the second DNA strand template. RNA can be amplified in vitro, in situ or in vivo.

Controls may be included within the sample to assure that amplification and labeling procedures do not change the true distribution of biomarker polynucleotides in a sample. For this purpose, a sample may be spiked with a known amount of a control biomarker polynucleotide, and the composition of probes includes reference probes which specifically hybridize with the control biomarker polynucleotides. After hybridization and processing, the hybridization signals obtained should accurately the amounts of control biomarker polynucleotide added to the sample.

The biomarker polynucleotides or polypeptides (including antibodies as discussed below) may be labeled with one or more labeling moieties to allow for detection of hybridized probe/biomarker complexes. The labeling moieties can include compositions that can be detected by spectroscopic, photochemical, biochemical, bioelectronic, immunochemical, electrical, optical or chemical means. The labeling moieties include radioisotopes, such as $^3H$, $^{14}C$, $^{32}P$, $^{33}P$ or $^{35}S$, chemiluminescent compounds, labeled binding proteins, heavy metal atoms, spectroscopic markers, such as fluorescent markers and dyes, magnetic labels, linked enzymes, mass spectrometry tags, spin labels, electron transfer donors and acceptors, and the like.

Nucleic acid labeling can be carried out during an amplification reaction, such as polymerase chain reactions and in vitro transcription reactions, or by nick translation or 5' or 3'-end-labeling reactions. When the label is incorporated after or without an amplification step, the label is incorporated by using terminal transferase or by phosphorylating the 5' end of the biomarker polynucleotide using, e.g., a kinase and then incubating overnight with a labeled oligonucleotide in the presence of T4 RNA ligase. Alternatively, the labeling moiety can be incorporated after hybridization once a probe/biomarker complex has formed.

Polypeptide labeling can be conducted using a variety of techniques well known in the art, and the choice of the technique(s) can be tailored to the polypeptide in question according to criteria known to one of skill in the art. Specifically, polypeptides can be fluorescently labeled with compounds such as FITC or rhodamin, essentially as described in Harlow and Lane, Antibodies: A Laboratory Manual, Cold Spring Harbor Laboratory, New York (1988), in particular pages 353-356, or with other fluorescent compounds such as nile red or 2-methoxy-2,4-diphenyl-3(2H) fur-anone (Daban, *Electrophoresis*, 2001, 22(5): 874-80). Polypeptides can also be labeled with a detectable protein such as GFP (detection based on fluorescence) or the vitamin biotin (detection with streptavidin). Polypeptides can also be radioactively labeled with the isotope $^{35}S$. Additional methods are widely known in the art.

In particular embodiments, cellular metabolites may be extracted as organic acids. In some embodiments, after gentle removal of culture medium from proliferating cells, or freezing medium from frozen viable samples, cells may be rapidly quenched with 80% methanol, chilled to −80° C., and then incubated at −80° C. for 15 min. Other alcohols that may be used for quenching include ethanol, isopropanol, etc. Extracts may subsequently transferred and centrifuged at 10,000-14,000 g for 15-20 min. at 4° C. The organic acid pool in the supernatant may be further purified by drying under nitrogen gas, redissolving in deionized water, and then elution from an AG-1 X8 100-200 anion exchange resin (Bio-Rad) in 3 N HCl after washing with five column volumes. After centrifugation at 10,000-14,000 g for 15-20 min at 4° C. to remove precipitated protein, supernatants may be dried under nitrogen gas.

In some embodiments, cold methanol is added to a patient sample for the quenching of metabolism and subsequent protein precipitation following a short centrifugation step. In some embodiment, other alcohols are added (e.g., ethanol, isopropanol, etc.). Following centrifugation, the aqueous supernatant layer contains the serum metabolites. Upon recovery of this layer, the metabolites can be made amenable to GC-MS analysis by addition of a chemical derivatization agent, such as N-methyl-N-tert-butyldimethylsilyltrifluoroacetamide (MTBSTFA), followed by a short heating period. The derivatized metabolites can then be injected and analyzed on the GC-MS instrument in electron ionization mode in approximately 30 minutes. In another embodiment, liquid chromatography-mass spectrometry ("LC-MS") methods may be used, which eliminate the need to perform a chemical derivatization step during sample preparation. The inclusion of a known quantity of an isotopically labeled 2HG into the patient sample at the beginning of the procedure can allow for absolute quantitation of 2HG abundance. Accordingly, analysis differentially produced 2HG can be used to generate a hypoxic profile, which can detect the presence of chronic hypoxia, monitor progression or abatement hypoxia, and/or monitor treatment response or optimization. Embodiments of the present invention further comprise the discovery that enzymatic assays may be used to measure 2HG levels as a marker of chronic hypoxia.

Measuring Nucleic Acid Levels

In certain embodiments, 2HG synthesis may be assayed in combination with other cellular and/or tissue biomarkers, thereby providing further clinically relevant data, or increased sensitivity and specificity of analysis. Furthermore, embodiments of the invention contemplate both direct and indirect assays of 2HG synthesis. Indirect assessments of 2HG synthesis include, for example, polynucleotide-based methods of assaying expression levels of one or more genes related to 2HG synthesis; e.g., IDH2. The polynucleotide sequences encoding biomarkers may be used in in-situ hybridization or RT-PCR assays of fluids or tissues from biopsies to detect abnormal gene expression. Such methods may be qualitative or quantitative in nature and may include Southern or Northern analysis, dot blot or other membrane-based technologies; PCR technologies; chip based technologies (for nucleic acid detection). All of these techniques are well known in the art and are the basis of many commercially available diagnostic kits.

Alternatively or additionally, such assays may be useful in evaluating the efficacy of a particular therapeutic treatment regimen. Such monitoring may generally employ a combination of body fluids or cell extracts taken from normal subjects or subjects suffering from acute hypoxia, either animal or human, under conditions suitable for hybridization or amplification. Standard hybridization may be quantified by comparing the values obtained for normal subjects with a dilution series of hypoxia marker gene products run in the same experiment where a known amount of purified gene product is used. Standard values obtained from normal samples may be compared with values obtained from samples from subjects affected by or suspected of being affected by acute hypoxia. Deviation between standard and subject values establishes the presence of disease.

Once chronic hypoxia is established, a therapeutic agent or treatment may be administered. As such, in certain embodiments of the invention, assays as described herein may be repeated on a regular basis to evaluate whether the values progress toward or return to the normal or standard pattern. Successive treatment profiles may be used to show the efficacy of treatment over a period of several days or several-months.

Polymerase Chain Reaction (PCR) may be used in specific embodiments. Appropriate oligonucleotide primers may be chemically synthesized or generated enzymatically or produced from a recombinant source. Oligonucleotides generally comprise two nucleotide sequences, one with sense orientation and one with antisense orientation, employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences. Methods of performing RT-PCR are standard in the art and the method may be carried out using commercially available kits. Other PCR techniques are well known to one of skill in the art, and include, for example, qPCR, real time PCR, reverse transcriptase PCR, PCR done in high density arrays, e.g., open arrays.

Alternatively or additionally, oligonucleotides or longer fragments derived from nucleic acids encoding each biomarker may be used as targets in a microarray. A number of different array configurations and methods of their production are known to those skilled in the art (see, for example, U.S. Pat. Nos. 5,445,934; 5,532,128; 5,556,752; 5,242,974; 5,384,261; 5,405,783; 5,412,087; 5,424,186; 5,429,807; 5,436,327; 5,472,672; 5,527,681; 5,529,756; 5,545,531; 5,554,501; 5,561,071; 5,571,639; 5,593,839; 5,599,695; 5,624,711; 5,658,734; and 5,700,637). Microarray technology allows for the measurement of the steady-state level of large numbers of polynucleotide sequences simultaneously. Microarrays currently in wide use include cDNA arrays and oligonucleotide arrays. Analyses using microarrays are generally based on measurements of the intensity of the signal received from a labeled probe used to detect a cDNA sequence from the sample that hybridizes to a nucleic acid probe immobilized at a known location on the microarray (see, for example, U.S. Pat. Nos. 6,004,755; 6,218,114; 6,218,122; and 6,271,002). Array-based gene expression methods are known in the art and have been described in numerous scientific publications as well as in patents (see, for example, M. Schena et al., Science, 1995, 270: 467-470; M. Schena et al., Proc. Natl. Acad. Sci. USA 1996, 93: 10614-10619; J. J. Chen et al., Genomics, 1998, 51: 313-324; U.S. Pat. Nos. 5,143,854; 5,445,934; 5,807,522; 5,837,832; 6,040,138; 6,045,996; 6,284,460; and 6,607,885).

Measuring Levels of Proteins and Products

In certain embodiments, protein levels may be measured. For example, antibodies may be used in characterizing biomarker content of healthy and hypoxic tissues, fluid samples or subjects through techniques such as ELISAs, immunohistochemical detection and Western blotting, which are discussed in more detail below.

Additionally, Embodiments of the invention encompass both direct and indirect assessments of 2HG levels. For example, the synthesis of 2HG may be assayed indirectly through detection of one or more enzymes products related to the synthesis of 2HG. For example, enzymatic assays for quantification of 2HG based on the detection of stoichiometrically generated NADH have been described previously (Balss, J. et al., *Acta Neuropathol.*, 2012 Nov. 2, incorporated herein by reference).

Particular embodiments of the invention use ELISA assays. For example, antibodies specific to IDH1/2, HIF1/2, or 2HG dehydrogenase or 2HG may be immobilized onto a selected surface, preferably a surface exhibiting a protein affinity such as the wells of a polystyrene microtiter plate. After washing to remove incompletely adsorbed material, it is desirable to bind or coat the assay plate wells with a non-specific protein that is known to be antigenically neutral with regard to the test antisera such as bovine serum albumin (BSA), casein or solutions of powdered milk. This allows for blocking of non-specific adsorption sites on the immobilizing surface and thus reduces the background caused by non-specific binding of antigen onto the surface. After binding of antibody to the well, coating with a non-reactive material to reduce background, and washing to remove unbound material, the immobilizing surface is contacted with the biological sample to be tested in a manner conducive to immune complex (antigen/antibody) formation.

Following formation of specific immunocomplexes between the test sample and the bound antibody, and subsequent washing, the occurrence and even amount of immunocomplex formation may be determined by subjecting same to a second antibody having specificity for the tumor marker that differs from the first antibody. Appropriate conditions preferably include diluting the sample with diluents such as BSA, bovine gamma globulin (BGG) and phosphate buffered saline (PBS)/Tween. These added agents also tend to assist in the reduction of nonspecific background. The layered antisera is then allowed to incubate for from about 2 to about 4 hr, at temperatures preferably on the order of about 25° C. to about 27° C. Following incubation, the antisera-contacted surface is washed so as to remove non-immunocomplexed material. A preferred washing procedure includes washing with a solution such as PBS/Tween, or borate buffer.

For convenient detection purposes, the second antibody may have an associated enzyme that will generate a color development upon incubating with an appropriate chromogenic substrate. For example, the second antibody-bound surface may be contacted and incubated with a urease or peroxidase-conjugated anti-human IgG for a period of time and under conditions which favor the development of immunocomplex formation (e.g., incubation for 2 hr at room temperature in a PBS-containing solution such as PBS/Tween).

After incubation with the second enzyme-tagged antibody, and subsequent to washing to remove unbound material, the amount of label is quantified by incubation with a chromogenic substrate such as urea and bromocresol purple or 2,2'-azino-di-(3-ethyl-benzthiazoline)-6-sulfonic acid (ABTS) and hydrogen peroxide, in the case of peroxidase as the enzyme-label. Quantitation is then achieved by measuring the degree of color generation, e.g., using a visible spectrum spectrophotometer. The preceding format may be altered by first binding the sample to the assay plate. Then, primary antibody is incubated with the assay plate, followed by detecting of bound primary antibody using a labeled second antibody with specificity for the primary antibody.

Immunoblotting and immunohistochemical techniques using antibodies directed against the hypoxia-related biomarkers are used in some embodiments. The antibodies may be polyclonal or monoclonal. The antibodies may be used as high-affinity primary reagents for the identification of proteins immobilized onto a solid support matrix, such as nitrocellulose, nylon or combinations thereof. In conjunction with immunoprecipitation, followed by gel electrophoresis, these antibodies may be used as a single step reagent for use in detecting antigens against which secondary reagents used in the detection of the antigen cause an adverse background. Immunologically-based detection methods for use in conjunction with Western blotting include enzymatically-, radiolabel-, or fluorescently-tagged secondary antibodies against the toxin moiety are considered to be of particular use in this regard.

Additionally and alternatively, as further discussed below, the protein and product expression levels may be determined using mass spectrometry-based methods or image (including use of labeled ligand)-based methods known in the art for the detection of proteins. Other suitable methods include 2D-gel electrophoresis and proteomics-based methods. Proteomics, which studies the global changes of protein expression in a sample, can include the following steps: (1) separation of individual proteins in a sample by electrophoresis (1-D PAGE), (2) identification of individual proteins recovered from the gel (e.g., by mass spectrometry or N-terminal sequencing), and (3) analysis of the data using bioinformatics.

As mentioned, 2HG levels may be ascertained either directly or indirectly via measurement of levels of related metabolites or products generated or consumed by 2HG production. For example, 2HG levels may be determined by a corresponding reduction in alpha-ketoglutarate levels. In another example, 2HG levels may be determined enzymatically by assessment of NADH levels. In a specific example, a sample comprising 2HG can be prepared in a buffer and enzyme that catalyze the oxidation of 2HG to alpha-ketoglutarate, which generates NADH. NADH can generate fluorescent reporter molecules from non-fluorescent precursors (e.g., Resazurin), whereby the level of fluorescence is directly quantifiable and correlated with 2HG levels.

Antibodies

Once a biomarker of choice is identified, one of skill in the art may produce antibodies against that marker using techniques well known to those of skill in the art. Thus, in some embodiments of the invention, antibodies are used or produced that are specific to 2HG or enzymes such as IDH2 that are responsible for the hypoxia-induced increase in 2HG synthesis or related to various hypoxic conditions. The antibodies may be used to detect the biomarkers in the screening and diagnostic methods of the invention.

Various procedures known in the art may be used for the production of antibodies. Antibodies of the invention include, but are not limited to, synthetic antibodies, monoclonal antibodies, recombinantly produced antibodies, intrabodies, multispecific antibodies (including bi-specific antibodies), human antibodies, humanized antibodies, chimeric antibodies, synthetic antibodies, single-chain Fvs (scFv) (including bi-specific scFvs), single chain antibodies Fab fragments, F(ab') fragments, disulfide-linked Fvs (sdFv), and anti-idiotypic (anti-Id) antibodies, and epitope-binding fragments of any of the above. In particular embodiments, antibodies of the present invention include immunoglobulin molecules and immunologically active portions of immunoglobulin molecules, i.e., molecules that contain an antigen binding site that immunospecifically binds to biomarkers of interest.

For production of the antibody, various host animals can be immunized by injection with 2HG, or derivatives thereof, or IDH2 or any other hypoxia-related antigen of interest. Such host animals include, but are not limited to, rabbits, mice, rats, etc. Various adjuvants can be used to increase the immunological response, depending on the host species, and include, but are not limited to, Freund's (complete and incomplete), mineral gels such as aluminum hydroxide, surface active substances such as lysolecithin, pluronic polyols, polyanions, peptides, oil emulsions, dinitrophenol, and potentially useful human adjuvants such as bacille Calmette-Guerin (BCG) and *Corynebacterium parvum*.

For preparation of monoclonal antibodies, any technique that provides for the production of antibody molecules by continuous cell lines in culture may be used. Such techniques include, but are not restricted to, the hybridoma technique originally developed by Kohler and Milstein (*Nature,* 1975,256:495-497), the trioma technique (Gustafsson et al., *Hum. Antibodies Hybridomas,* 1991, 2:26-32), the human B-cell hybridoma technique (Kozbor et al., *Immunology Today,* 1983, 4:72), and the EBV hybridoma technique to produce human monoclonal antibodies (Cole et al., In: Monoclonal Antibodies and Cancer Therapy, Alan R. Liss, Inc., 1985, pp. 77-96).

According to the present invention, human antibodies may be used and can be obtained by using human hybridomas (Cote et al., *Proc. Natl. Acad. Sci. USA,* 1983, 80:2026-2030) or by transforming human B cells with EBV virus in vitro (Cole et al, In: Monoclonal Antibodies and Cancer Therapy, Alan R. Liss, Inc., 1985, pp. 77-96). In some embodiments of the invention, techniques developed for the production of "chimeric antibodies" (Morrison et al., *Proc. Natl. Acad. Sci. USA*, 1984, 81:6851-6855; Neuberger et al., *Nature*, 1984, 312:604-608; Takeda et al, *Nature*, 1985, 314:452-454) by splicing the genes from a mouse antibody molecule specific for a biomarker together with genes from a human antibody molecule of appropriate biological activity can be used; such antibodies are within the scope of this invention.

Antibodies for use in embodiments of the invention can also be identified and isolated from human antibody libraries. For example, expression products of a polynucleotide library encompassing the theoretical diversity of mouse, rabbit, goat or human antibodies (e.g., $10^{12th}$ different antibodies), or physically realizable subportion thereof, can be screened with the totality and/or antigenic portions of 2HG to identify novel interacting antibodies or fragments. Exemplary libraries include phage-display libraries from immunized individuals (see, e.g., Barbas et al., *J. Mol. Biol.*, 1993, 230:812-823), libraries of germline sequences (Griffiths et al., *EMBO J.*, 1994, 13: 3245-3260) or naïve B-cell repertoires (Vaughan et al., *Nat. Biotech.*, 1996, 14:309-314).

Synthetic libraries, in which germline antibody gene segments (VH, DH, and JH or Vκ/λ and Jκ/λ) are cloned and arranged combinatorially in vitro so as to reconstitute genes encoding complete VH and VL chains (see, e.g., Winter, *FEBS Letters*, 1998, 430:92-94), may also be used. See, e.g., de Kruif et al., *J. Mol. Biol.*, 1995, 248: 97-105; Griffiths et al., *EMBO J.*, 1994, 13: 3245-3260; Hoogenboom and Winter, *J. Mol. Biol.*, 1992, 227:381-388; and Nissim et al., *EMBO J.*, 1994, 13:692-698. Semi-synthetic libraries, which are generated by selecting one or more antibody frameworks as a scaffold and randomizing sequences within the CDR loops, may also be used. Particular libraries may have fully or partially randomized CDR3 hypervariable regions of the heavy and/or light chains (see, e.g., Huls et al., *Nat. Biotech.*, 1999, 17:276-281; and Knappik et al. (*J. Mol. Biol.*, 2000, 296: 57-86). See generally, Fuh, G. *Expert. Opin. Biol. Ther.*, 2007, 7(1): 73-87; Kim et al., *Mol. Cells*, 2005, 20(1): 17-29. Phage, yeast, *E. coli* and ribosome display technologies may be used for library screening.

According to certain embodiments of the present invention, techniques described for the production of single chain antibodies can be adapted to produce specific antibodies. Antibody fragments that contain the idiotypes of 2HG can be generated by techniques known in the art. For example, such fragments include, but are not limited to, the F(ab')2 fragment which can be produced by pepsin digestion of the antibody molecule; the Fab' fragment that can be generated by reducing the disulfide bridges of the F(ab')2 fragment; the Fab fragment that can be generated by treating the antibody molecular with papain and a reducing agent; and Fv fragments. Synthetic antibodies, e.g., antibodies produced by chemical synthesis, are useful in the present invention.

Methods for detecting the presence of 2HG either directly or indirectly through detection of enzymes (e.g., IDH2) or product related to the synthesis of 2HG, may be accomplished via immuno-based identification techniques known in the art, as discussed above. Exemplary immunoassays include time resolved fluorescence immunoassays (TR-FIA), radioimmunoassays, enzyme immunoassays (e.g., ELISA), immunofluorescence immunoprecipitation, latex agglutination, hemagglutination, Western blot, and histochemical tests, which are conventional methods well-known in the art. As will be appreciated by one skilled in the art, the immunoassay may be competitive or non-competitive. Methods of detection and quantification of the signal generated by the complex formed by binding of the binding agent with the protein marker will depend on the nature of the assay and of the detectable moiety (e.g., fluorescent moiety).

Particular embodiments of the invention utilize commercially available 2HG (e.g., Abgent, Proteintech, Fisher Scientific, Novatein, etc.) and/or IDH2 antibodies (e.g., Abcam, ab55271). Additional embodiments encompass of the use of other commercially available antibodies specific for binding enzymes directly or indirectly associated with 2HG synthesis; for example, IDH1, 2HG dehydrogenase, pyruvate dehydrogenase and the major enzymes of the TCA cycle such as alpha-ketoglutarate dehydrogenase, aconitase, citrate synthase, succinyl CoA synthetase, and others.

Generation of Hypoxic Profiles

The methods of the present invention may be used to generate a profile of various biomarkers, including 2HG, that serves as a specific diagnostic for chronic hypoxia. In essence, a hypoxic profile is like a fingerprint that may be used to classify a subject as either positive or negative for chronic hypoxia. Diagnosis may be made by comparison to a reference biomarker profile, for example, from a population of subjects selected from a group comprising normal, healthy or normoxic subjects, subjects known to suffer from chronic hypoxia, subjects known to suffer from acute hypoxia, or subjects who are suffering from an onset of chronic or acute hypoxia. Thus, a given hypoxic profile may diagnose whether a subject is suffering from acute or chronic hypoxia. Additionally or alternatively, the hypoxic profile may diagnose the severity of chronic hypoxia (e.g., from mild to severe). In embodiments of the present invention, a subject's hypoxic profile may include assessment of 2HG and optionally may include assessment of one or more additional biomarkers, such as assessment of IDH1/2, HIF1/2, or 2HG dehydrogenase gene or protein expression.

Generation of a hypoxic profile requires detection of the one or more biomarkers that comprise the profile. The present invention provides the particular insight that technologies described herein are particularly useful for the detection and/or quantitation of biomarker levels in clinical settings. Detection technologies include, without limitation, IR (infrared spectroscopy), NMR (nuclear magnetic resonance), including variations such as correlation spectroscopy (COSY), nuclear Overhauser effect spectroscopy (NOESY), and rotating frame nuclear Overhauser effect spectroscopy (ROESY), and Fourier Transform, 2-D PAGE technology, Western blot technology, ELISA, tryptic mapping, in vitro biological assay, immunological analysis, LC-MS (liquid chromatography-mass spectrometry), and GC-MS (gas chromatography-mass spectrometry).

In certain embodiments 2HG assessment and the hypoxic profile are generated, at least in part, through mass spectrometry. Mass spectrometry methods known to those of skill in the art and suitable for use in embodiments of the present invention include electrospray ionization mass spectrometry (ESI-MS), ESI-tandem mass spectrometry, matrix-assisted laser desorption ionization time-of-flight mass spectrometry (MALDI-TOF-MS), surface-enhanced laser desorption/ionization time-of-flight mass spectrometry (SELDI-TOF-MS), desorption/ionization on silicon (DIOS), secondary ion mass spectrometry (SIMS), quadrupole time-of-flight (Q-TOF), atmospheric pressure chemical ionization mass spectrometry (APCI-MS), APCI-MS/MS; APCI-(MS), atmospheric pressure photoionization mass spectrometry (APPI-MS), APPI-MS/MS, and APPI-(MS). Other mass spectrometry methods may include, among others, quadrupole, fourier transform mass spectrometry (FTMS) and ion trap. Mass spectrometry may be used alone or in combination one or more separation methods. These include chromatographic separation methods such as thin-layer, gas or liquid chromatography, or any combination thereof. In some embodiments, a biological sample may be separated by gas chromatography followed by mass spectrometry analysis.

In some embodiments of the invention, the sample may be delivered directly to the detection device without preparation and/or separation beforehand. In another embodiment of the invention, once prepared and/or separated, the metabolic products are delivered to a detection device, which detects them in a sample. In another embodiment of the invention, metabolic products in elutions or solutions are delivered to a detection device by electrospray ionization (ESI). In yet another embodiment of the invention, nanospray ionization (NSI) is used. Nanospray ionization is a miniaturized version of ESI and provides low detection limits using extremely limited volumes of sample fluid. In additional embodiments, microfluidic devices may be used in conjunction with ionization techniques to provides samples to the detection device at flow rates and complexity levels that are optimal for detection. Furthermore, a microfluidic device may be aligned with a detection device for optimal sample capture.

In particular embodiments, gas chromatography-mass spectroscopy (GC-MS) may be used. Appropriate procedures are known to those of skill in the art. For example, after drying, samples may be redissolved in a 1:1 mixture of acetonitrile and N-methyl-N-tert-butyldimethylsilyltrifluoroacetamide (MTBSTFA) and heated for 1 hr at 60° C. to derivatize prior to GC-MS analysis. In other embodiments, any derivatization agent known to those of skill in the art may be used. Samples may be injected into an Agilent 7890A GC with an HP-5MS capillary column, connected to an Agilent 5975C Mass selective detector operating in splitless mode using electron impact ionization with ionizing voltage of −70 eV and electron multiplier set to 1060 V. In some embodiments, the GC temperature may be started at approximately 100° C. for 3-5 min, ramped to approximately 230° C. at 4° C./min and held for 4-6 min, then ramped to 300° C. and held for 5-10 min. Mass range of 50-500 amu may be recorded at 2.71 scans/s. Isotopic enrichment in citric acid may be monitored using ions at m/e-463 and 464 for citrate +4 and citrate +5 (containing 4 and 5 $^{13}$C-enriched atoms, respectively), formed through loss of a t-butyl (−57 amu) and t-butyldimethylsilanol (−132 amu) from the molecular ion tetra-TBDMS-citric acid (648 amu). Isotopomer distributions may simultaneously corrected for naturally occurring heavy isotopes of all elements in each mass fragment using a correction matrix as previously described (Weckwerth, 2007). Identification of the 2HG metabolite peak can confirmed using standards obtained from Sigma or any other suitable standard. 2HG and glutamate signal intensities may quantified by integration of peak areas or other appropriate areas.

In some embodiments, liquid chromatography-mass spectrometry may be used. In some embodiments, organic acids from cellular extracts are purified from a sample, followed by evaporation to dryness under nitrogen. After redissolving samples in deionized water, citrate may be detected on two or more different liquid chromatography (LC) MS approaches, all of which give comparable results. LC separation may be achieved by reversed phase chromatography using tributylamine as an ion pairing agent with ionization by negative electrospray at 23 kV. In one embodiment, the approach uses a Thermo Discovery Max triple quadrupole mass spectrometer in multiple reaction monitoring mode, with citrate quantified using the reaction 191→87 at 20 eV. Additional reactions for every possible labeled form of citrate may also be monitored using variations of the same transition. Reactions used to monitor other TCA components have been described previously. An alternative MS approach in particular embodiments uses a Thermo Exactive Orbitrap mass spectrometer operated at 100,000 mass resolving power, with citrate and its isotope-labeled forms be quantified based on extracted ion chromatograms at their exact masses.

Certain embodiments of the invention utilize quantitative mass spectrometry techniques. Such techniques allow for the absolute quantification of hypoxic severity and allow for direct comparison to one or more reference or baseline (e.g., normoxic) populations. Quantitative techniques used in embodiments of the invention include both labeled techniques (e.g., tandem mass tagging) and non-labeled techniques. Quantitative mass spectrometry is known to those of skill in the art as described in Bantscheff, M. et al. "Quantitative mass spectrometry in proteomics: a critical review", Anal. Bioanal. Chem., 2007, 389:1017-1031 and Want, E. J. et al. "The expanding role of mass spectrometry in metabolite profiling and characterization", Chem. Bio. Chem., 2005, 6:1941-1951, incorporated herein by reference.

In some embodiments, enzymatic assays are used to measure biomarker levels. As mentioned, 2HG levels and the levels of other biomarkers may be ascertained either directly or indirectly via measurement of levels of related metabolites or products generated or consumed by 2HG production. For example, 2HG levels may be determined by a corresponding reduction in alpha-ketoglutarate levels. In another example, 2HG levels may be determined enzymatically by assessment of NADH levels. In a specific example, a sample comprising 2HG can be prepared in a buffer and enzyme that catalyze the oxidation of 2HG to alpha-ketoglutarate, which generates NADH. NADH can generate fluorescent reporter molecules from non-fluorescent precursors (e.g., Resazurin), whereby the level of fluorescence is directly quantifiable and correlated with 2HG levels.

As discussed above, in particular embodiments of the invention, multiple biomarkers, including 2HG, are measured to generate a hypoxic profile. The use of multiple biomarkers increases the predictive value of the analyses and provides greater utility in diagnosis, predictive assessments, patient stratification and patient monitoring. In certain embodiments, pattern recognition processes may be used to detect patterns formed by multiple biomarkers, or the temporal changes in a single biomarker (e.g., 2HG), which greatly improves the sensitivity and specificity of clinical diagnosis. Subtle variations in data from clinical samples, e.g., obtained using the mass spectroscopy techniques discussed above, indicate that certain patterns of protein expression or metabolite synthesis can predict phenotypes such as chronic hypoxia and chronic hypoxia vs. acute hypoxia.

Data Analysis

Once the expression levels of 2HG or other biomarkers of interest have been determined (as described above) for a biological sample being analyzed, they can either be directly correlated to hypoxic or normoxic conditions or be compared to the production levels, activity levels, and/or expression levels in one or more control samples. Comparison of levels according to embodiments of the present invention is preferably performed after the levels obtained have been corrected for both differences in the amount of sample assayed and variability in the quality of the sample used (e.g., amount of protein extracted, amount of tissue, or amount and quality of mRNA tested). Correction may be carried out using different methods well-known in the art. For example, the protein concentration of a sample may be standardized using photometric or spectrometric methods or gel electrophoresis (as already mentioned above) before the sample is analyzed. In case of samples containing nucleic acid molecules, correction may be carried out by normalizing the levels against reference genes (e.g., housekeeping genes like 18S rRNA) in the same sample. Alternatively or additionally, normalization can be based on the mean or median signal (e.g., Ct in the case of RT-PCR) of all assayed genes or a large subset thereof (global normalization approach).

In particular embodiments, when the sample is measured and data is generated, e.g., by mass spectrometry, the data is then analyzed by a computer software program. Generally, the software can comprise code that converts signal from the mass spectrometer into computer readable form. The software also can include code that applies an algorithm to the analysis of the signal to determine whether the signal represents a "peak" in the signal corresponding to a marker of this invention, or other useful markers. The software also can include code that executes an algorithm that compares signal from a test sample to a typical signal characteristic of "normal" and hypoxic, or acute vs. chronic hypoxia, and determines the closeness of fit between the two signals. The software also can include code indicating which the test sample is closest to, thereby providing a probable diagnosis.

In particular embodiments of the invention, a decision rule may be used to diagnose or classify the hypoxic state of a subject. This rule can take on one or more forms that are known in the art, as exemplified in Hastie et al., in "The Elements of Statistical Learning," Springer-Verlag (Springer, N.Y. (2001)), herein incorporated by reference in its entirety. Analysis of biomarkers in the complex mixture of molecules within the sample generates features in a data set. A decision rule may be used to act on a data set of features to diagnose chronic hypoxia, evaluate the status or response to treatment of known chronic hypoxia, or to differentiate chronic hypoxia from acute hypoxia.

The application of the decision rule does not require perfect classification. A classification may be made with at least about 90% certainty. In other embodiments, the certainty is at least about 80%, at least about 70%, or at least about 60%. The useful degree of certainty may vary, depending on the particular method of the present invention. "Certainty" is defined as the total number of accurately classified individuals divided by the total number of individuals subjected to classification. As used herein, "certainty" means "accuracy." Classification may also be characterized by its "sensitivity." The "sensitivity" of classification relates to the percentage of subjects suffering from acute hypoxia who were correctly identified as such. "Sensitivity" is defined in the art as the number of true positives divided by the sum of true positives and false negatives. In contrast, the "specificity" of embodiments of the invention may be defined as the percentage of patients who were correctly identified not suffering from chronic hypoxia. That is, "specificity" relates to the number of true negatives divided by the sum of true negatives and false positives. In one embodiment, the sensitivity and/or specificity is at least 90%, at least 80%, at least 70% or at least 60%. The number of features that may be used to classify an individual with adequate certainty is at least one; typically 2HG. As discussed above in reference to measurement of combinations of biomarkers, the number of features that may be used to classify an individual is optimized to allow classification of an individual with high certainty.

The decision rule can comprise a data analysis algorithm, such as a computer pattern recognition algorithm. Other suitable algorithms include, but are not limited to, logistic regression or a nonparametric algorithm that detects differences in the distribution of feature values (e.g., a Wilcoxon Signed Rank Test). The decision rule may be based upon one, two, three, four, five, 10, 20 or more features. Applying the decision rule may also comprise using a classification tree algorithm. For example, the reference biomarker profile may comprise at least three features, where the features are predictors in a classification tree algorithm. The data analysis algorithm predicts membership within a population (or class) with an accuracy of at least about 60%, at least about 70%, at least about 80% and at least about 90%.

Suitable algorithms are known in the art. Such algorithms classify complex spectra from biological materials, such as a blood or tumor sample, to distinguish individuals as normal or as possessing biomarker expression levels characteristic of a particular disease state; e.g., chronic hypoxia. While such algorithms may be used to increase the speed and efficiency of the application of the decision rule and to avoid investigator bias, one of ordinary skill in the art will realize that computer-based algorithms are not required to carry out the methods of the present invention.

Algorithms may be applied to the comparison of hypoxic profiles, regardless of the method that was used to generate the profile. For example, suitable algorithms can be applied to biomarker profiles generated using gas chromatography, as discussed in Harper, "Pyrolysis and GC in Polymer Analysis,", 1985, Dekker, N.Y. Further, Wagner et al., *Anal. Chem.*, 2002, 74: 1824-35 disclose an algorithm that improves the ability to classify individuals based on spectra obtained by static time-of-flight secondary ion mass spectrometry (TOF-SIMS). Fresenius J., *Anal. Chem.*, 2000, 366: 701-11 discusses the use of MALDI-TOF-MS and liquid chromatography-electrospray ionization mass spectrometry (LC/ESI-MS) to classify profiles of biomarkers in complex biological samples.

Additional embodiments may utilize any known classification model to identify biomarker trends and determine the hypoxic profile of a subject. Classification models can be formed using any suitable statistical classification (or "learning") method that attempts to segregate bodies of data into classes based on objective parameters present in the data. Classification methods may be either supervised or unsupervised. Examples of supervised and unsupervised classification processes are described in Jain, "Statistical Pattern Recognition: A Review", IEEE Transactions on Pattern Analysis and Machine Intelligence, Vol. 22, No. 1, January 2000, which is herein incorporated by reference.

In supervised classification, training data containing examples of known categories are presented to a learning mechanism, which learns one more sets of relationships that define each of the known classes. New data may then be applied to the learning mechanism, which then classifies the new data using the learned relationships. Examples of supervised classification processes include linear regression processes (e.g., multiple linear regression (MLR), partial least squares (PLS) regression and principal components regression (PCR)), binary decision trees (e.g., recursive partitioning processes such as CART—classification and regression trees), artificial neural networks such as back propagation networks, discriminant analyses (e.g., Bayesian classifier or Fischer analysis), logistic classifiers, and support vector classifiers (support vector machines).

Diagnosis of Chronic Hypoxia

Embodiments of the invention are based on the surprising discovery that 2HG levels, optionally assayed in conjunction with one or more additional biomarkers, can diagnose chronic hypoxia, distinguish between different sub-types of hypoxia, distinguish between chronic and acute hypoxia, and determine the severity of the hypoxia, and/or assess risk for developing chronic hypoxia. Accordingly, in some embodiments, the present invention provides methods for analyzing biological samples obtained from a subject suspected of having chronic hypoxia to measure 2HG levels, and optionally expression levels of other biomarkers described herein, to determine if the subject has chronic hypoxia, is at risk of developing chronic hypoxia, or to determine the severity of chronic hypoxia.

As described above, the biomarkers' levels determined or measured for a biological sample obtained from the subject may be compared to one or more control levels. Various control levels of the biomarkers may be used. For example, suitable control levels may be indicative of the levels of the one or more biomarkers in a control subject who is normoxic. Such control levels may be obtained by measuring the corresponding one or more biomarkers simultaneously under same conditions in a control sample obtained from one or more healthy (e.g., normoxic) control subjects. Suitable control samples may be obtained from one healthy control individual or pooled from a plurality of healthy control individuals. In some embodiments, a control level indicative of the level of a biomarker in healthy individuals can be determined from a significant number of individuals, and an average or mean is obtained. In other embodiments, the control samples may be obtained from an acutely hypoxic individual or pooled from a plurality acutely hypoxic individuals. Typically, either the healthy control individual(s) or the acutely hypoxic individual(s) are at a comparable age or other development state relative to the suspected chronically hypoxic individual.

In some embodiments, a suitable control level for a biomarker is a numerical reference based on historical data, also referred to as a historical control (i.e., of a test or assay performed previously, or an amount or result that is previously known). In some embodiments, a control level is or comprises a printed or otherwise saved record. In some embodiments, an elevated level with statistical significance of the one or more biomarkers as compared to a suitable control level indicates that the subject has chronic hypoxia or is at risk of developing chronic hypoxia. In some embodiments, an increased (e.g., 2HG) or diminished level with statistical significance of the one or more biomarkers as compared to a suitable control level indicates that the subject has chronic hypoxia or is at risk of developing chronic hypoxia.

Various statistical techniques and analysis methods may be used to determine if a biomarker has an elevated or diminished level with statistical significance (i.e., the difference is not caused by random variations). Exemplary statistical techniques and methods include, but are not limited to, Linear and Quadradic discriminant analysis, k-nearest neighbor, independent t-test, chi square analysis, calculation of correlation coefficients and confidence intervals, and ANOVA. In some embodiments, a biomarker such as 2HG has an elevated level if the level of the biomarker measured in biological samples is more than 20%, 30%, 40%, 50%, 60%, 70%, 80%, 90%, 1-fold, 1.2-fold, 1.5-fold, 1.75-fold, 2-fold, 2.25-fold, 2.5-fold, 2.75-fold, or 3-fold higher as compared to a control level. In other embodiments, a biomarker has a diminished level if the level of the biomarker measured in biological samples is reduced by more than 10%, 20%, 30%, 40%, 50%, 60%, 70%, 80%, 90%, or 95% as compared to a control level.

In some embodiments, control levels indicative of the levels of the corresponding one or more biomarkers in a control subject who is suffering from chronic hypoxia may be used. Such control levels may be determined by measuring the corresponding one or more biomarkers simultaneously under the same conditions in control samples obtained from a control individual or pooled from a plurality of control individuals. In some embodiments, a control level indicative of the level of a biomarker in individuals suffering from chronic hypoxia can be determined from a significant number of individuals, and an average or mean is obtained.

In some embodiments, a suitable control level may be a numerical threshold established based on historical data (i.e., of a test or assay performed previously, or an amount or result that is previously known) that correlates with a subject who has chronic hypoxia, or is at risk of developing chronic hypoxia. In these embodiments, a substantially similar level within statistic error margin or, an elevated or diminished level with statistical significance, of the one or more biomarkers measured in a biological sample as compared to a suitable control level indicates that the subject has chronic hypoxia, or is at risk of developing chronic hypoxia.

In some embodiments, 2HG has a statistically significant elevated level indicative of chronic hypoxia when the level of 2HG measured in one or more biological samples is more than 20%, 30%, 40%, 50%, 60%, 70%, 80%, 90%, 1-fold, 1.2-fold, 1.5-fold, 1.75-fold, 2-fold, 2.25-fold, 2.5-fold, 2.75-fold, or 3-fold higher as compared to a control level. In some embodiments, the elevated level is statistically significant when it is associated with a P value less than 0.05, less than 0.01 or less than 0.001. Control levels may be obtained by measuring 2HG simultaneously under the same conditions in a control sample obtained from one or more healthy (e.g., normoxic) control subjects. Control samples may be obtained from one healthy control individual or pooled from a plurality of healthy control individuals. In some embodiments, control levels may be determined from a significant number of individuals, and an average or mean is obtained. In some embodiments, control samples may be obtained from an acutely hypoxic individual or pooled from a plurality acutely hypoxic individuals. Control levels may also be obtained from control subject known to be suffering from chronic hypoxia.

Those of skill in the art will appreciate that different tissues may require individual controls; in other words that in some embodiments it is necessary to compare one type of tissue to the same type of tissue. Those of skill in the art will also appreciate that, in practice, the level of 2HG indicative of chronic hypoxia may vary somewhat from subject to subject. For example, levels of 2HG indicating chronic hypoxia in a neonate may be different than hypoxic levels in an adult subject. Variables impacting 2HG levels include the age, the duration of the chronic hypoxia, body mass, diet, sex, altitude, metabolic activity and the tissue from which the sample is obtained.

In some embodiments, elevated or diminished levels of one or more biomarkers in a biological sample may be used to determine the severity of chronic hypoxia. In some embodiments, the elevated or diminished levels of one or more biomarkers are quantified in order to determine the severity and/or stage of chronic hypoxia.

Diagnosis of chronic hypoxic may occur in any appropriate patient population. Symptoms or signs may be non-specific and include, for example: neovascularization, dyspnea, restlessness, palpitations, confusion, agitation, headache, tremor, asterixis, diaphoresis, respiratory distress, cyanosis, tachycardia, thacypnea, cardiac dysrhythmias, hypertension, hypotension, lethargy and coma. Applicable patient populations include geriatric patients as well as pre-neonates, ante-neonates and postnatal infants. For example, 2HG may be used as a biomarker of chronic hypoxia in neonates with anatomical, pulmonary or cardiovascular complications that are suspected of impacting $O_2$ saturation on a long-term basis. As another example, 2HG biomarker levels may be measured to assist in the diagnosis or severity assessment of chronic obstructive pulmonary disease.

Once chronic hypoxia is established (or, in some embodiments, suspected or predicted), a therapeutic agent or treatment may be administered. As such, in certain embodiments of the invention, assays as described herein may be repeated on a regular basis to evaluate whether the values progress toward or return to the normal or standard pattern. Successive treatment profiles may be used to show the efficacy of treatment over a period of several days or several-months.

Identifying or Monitoring Treatment

The present invention further provides methods for evaluating the effectiveness of a therapy, monitoring responsiveness to therapy, prognosis for disease course, and measurement of disease progression in a subject. Typically, in such methods, levels of suitable biomarkers (e.g., 2HG) determined for a biological sample obtained from the subject from one or more time points are compared to the levels from the subject from one or more other time points. For example, biomarker levels may be measured before or at the beginning of a treatment course. Biomarker levels may be measured at one or more time points throughout the course of treatment and compared with the level before the treatment or from an earlier time point of a treatment course. Identification or selection of appropriate treatment, determining if a patient has positive response to a treatment and/or optimization of the treatment can be guided using the information obtained in these methods.

For example, using methods described herein, skilled physicians may select and prescribe treatments adapted to each individual patient based on the diagnosis and disease staging provided to the patient through determination of the levels, expression and/or activity levels of one or more biomarkers described herein (e.g., 2HG). In particular, the present invention provides physicians with a means of diagnosis of chronic hypoxia in individuals who manifest no overtly clinical symptoms of chronic hypoxia. Additional, embodiments of the present invention allow for diagnosis of chronic versus acute hypoxia, which will allow for application of the correct treatment and selectively narrow the range of potential underlying causes. For example, without wishing to be bound by any particular theory, elevated levels of 2HG may be specific to chronic hypoxia because acute hypoxia is a temporary condition of short duration in which 2HG levels do not have time to increase significantly above control levels. Correct diagnosis of chronic vs. acute hypoxia may also allow for application of suitable prophylactic treatments to prevent onset of related disease states.

In some embodiments, inventive methods described herein can be used for monitoring treatment response in a subject with chronic hypoxia. Typically, for example, the levels of one or more biomarkers in a subject with chronic hypoxia are measured after receiving treatment for directly for chronic hypoxia and/or for a condition identified or suspected as a primary cause of chronic hypoxia (e.g., obstructive pulmonary disease). The measured levels are then compared to a control level to determine if the subject with chronic hypoxia has positive response to the treatment. As used herein, a "positive response" to a treatment includes reduced severity of disease symptoms, slowed progression, abatement or cure of the disease. A suitable control level may be the level of the one or more biomarkers (e.g., 2HG levels) obtained from the same patient before receiving the treatment or measured at an earlier time point of the treatment.

In some embodiments, a suitable control level is the level of the one or more biomarkers in a control patient without the treatment. As mentioned above, in some embodiment the control patient is the subject about to undergo treatment. In some embodiments, control levels may be determined from a significant number of control patients, and an average or mean is obtained. Typically, a control patient is at a comparable disease or developmental stage. Typically, a diminished or elevated level with statistical significance of the one or more biomarkers as compared to a suitable control level indicates that the patient has positive response to the treatment. For example, a diminished level of 2HG relative to pre-treatment levels may indicate a positive response to treatment. Various statistical methods and techniques such as those described above may be used to determine statistical significance. In some embodiments, a biomarker has a diminished level indicating a positive response to therapy if the level of the biomarker measured in a biological sample obtained at a relevant time point of interest is reduced by more than 10%, 20%, 30%, 40%, 50%, 60%, 70%, 80%, 90%, 95% as compared to a control level. In some embodiments, a biomarker has an elevated level indicating a positive response to therapy if the level of the biomarker measured in biological samples is more than 20%, 30%, 40%, 50%, 60%, 70%, 80%, 90%, 1-fold, 1.2-fold, 1.5-fold, 1.75-fold, 2-fold, 2.25-fold, 2.5-fold, 2.75-fold, or 3-fold higher as compared to a control level. In some embodiments, 2HG has a statistically significant decreased level indicative of a positive response to therapy when the level of 2HG measured in one or more biological samples is more than 20%, 30%, 40%, 50%, 60%, 70%, 80%, 90%, 1-fold, 1.2-fold, 1.5-fold, 1.75-fold, 2-fold, 2.25-fold, 2.5-fold, 2.75-fold, or 3-fold lower as compared to a control level. In some embodiments, the decreased level is statistically significant when it is associated with a P value less than 0.05, less than 0.01 or less than 0.001.

Particular treatments that may be applied in embodiments of the invention include supplemental oxygen therapy, transfusion of packed red blood cells, caffeine, vitamin therapy, mechanical ventilation, positive pressure therapy, physical exercise, and surgical intervention (e.g. alleviation of airway obstruction or tracheotomy). Those of skill in the art will appreciate that these may be direct treatments for chronic hypoxia and/or for a condition identified or suspected as a primary cause of chronic hypoxia (e.g., obstructive pulmonary disease). Primary or underlying causes of chronic hypoxia may include chronic obstructive pulmonary disorder, airway obstruction, acute respiratory distress syndrome, pneumonia, pneumothorax, emphysema, congenital heart defects, pulmonary embolism, pulmonary edema, asthma, cystic fibrosis and high altitude.

In some embodiments, 2HG may be used as a biomarker to determine whether a subject is a suitable candidate for administration of a treatment. In a particular example, 2HG may serve as a companion diagnostic or predictive biomarker for administration of hypoxia-activated or hypoxia-inducible prodrugs. Hypoxia occurs in solid tumors and represents an attractive therapeutic option in oncology.

Prodrugs that are selectively activated within hypoxic cells or tissues are one mechanism of exploiting tumor hypoxia. Thus, embodiments of the invention include methods of screening tumor samples or samples from cancer patients for preferential susceptibility to treatment with hypoxia-inducible prodrugs. Likewise, embodiments of the invention include methods of identifying patients or patient populations who may benefit from treatment with hypoxia-inducible prodrugs.

Hypoxia-inducible prodrugs for use in embodiments of the invention include nitroimidazoles (e.g., TH-302 and NLCQ-1), dinitrobenzamides (e.g., PR-104, SN23862), tirapazamine and tirapazamine analogs (e.g., SN30000, SN29751 and AQ4N). Additional classes of hypoxia-inducible prodrugs for use in embodiments of the invention include nitrobenzyl phosphoramidate mustards, nitroheterocyclic methylquaternary salts, cobalt(III) complexes and indoloquinones.

In general, 2HG may be used as companion diagnostic for any drug or prodrug where hypoxia-selective cytotoxicity requires one-electron reduction of a relatively non-toxic prodrug to a radical that then becomes a substrate for back oxidation by oxygen to the original compound, thereby forming radicals or downstream products of radicals that are more toxic than the superoxide generated by redox cycling in cells. Embodiments of the invention are applicable to any cancer that forms solid tumors, including breast, colon, lung, prostate, liver and brain. In general, a tumor sample may be susceptible to treatment with hypoxia-inducible prodrugs when the level of 2-hydroxyglutarate is more than 20%, 30%, 40%, 50%, 60%, 70%, 80%, 90%, 1-fold, 1.2-fold, 1.5-fold, 1.75-fold, 2-fold, 2.25-fold, 2.5-fold, 2.75-fold, or 3-fold higher as compared to a control sample. Control samples may be obtained from tissue surrounding or adjacent to the tumor. Control samples may also be obtained as a median or mean measurement of one or more similar tissues from a population of healthy individuals. "Similar tissues", as used herein, may refer to tissues derived from the same stem cell lineage (e.g., endoderm, mesoderm, ectoderm or primordial germ cells).

Those of skill in the art will also appreciate that hypoxic states may be found both within the tumor (intra-tumoral) and in adjacent or nearby tissues. For example . . . chronic hypoxia may be caused by consumption and depletion of oxygen by tumor cells between blood capillaries and the hypoxic regions. Thus, samples for measurement of 2HG levels to determine whether a tissue is hypoxic (e.g., for determination of whether a subject is a candidate for hypoxia-inducible prodrugs) may be obtained from a tumor itself or nearby tissue.

The invention will be more fully understood by reference to the following examples. They should not, however, be construed as limiting the scope of the invention. All literature citations are incorporated by reference.

EXAMPLES

Example 1

Materials and Methods

SF188 and RCC4 cells were cultured in Dulbecco's Modified Eagle's Medium (DMEM; Invitrogen 11965), 10% fetal bovine serum (FBS; Gemini Biosystems), 100 units/ml Penicillin, 100 ug/ml Streptomycin, 25 mM glucose, and 6 mM L-glutamine. For glutamine starvation experiments, DMEM without glutamine (Invitrogen 11960) was supplemented with 10% dialyzed FBS (Gemini). For metabolic tracing experiments, DMEM without glutamine and with 10% dialyzed FBS was supplemented with [U-13C]-L-glutamine (Isotec 605-166). DMEM without glucose (Sigma) was supplemented with [U-13C]-D-Glucose (Cambridge Isotope Laboratories CLM-1396). Viability was determined by trypan blue exclusion. Hypoxia was generated using an InVivo2 400 hypoxic work station (Biotrace).

Cellular organic acids were extracted as previously described in Bennett B D, Yuan J, Kimball E H, & Rabinowitz J D (2008), "Absolute quantitation of intracellular metabolite concentrations by an isotope ratio-based approach", *Nat Protocols* 3:1299. Briefly, after the labeling period, the medium was gently aspirated and the cells were rapidly quenched with 80% methanol chilled to −80° C. After a 15 min incubation at −80° C., the extract was transferred and spun down at 10,000 rpm for 15 min at 4° C. The cellular organic acid pool in the supernatant was recovered and dried under nitrogen gas. Organic acids were purified by redissolving the dried extract in 1 ml of deionized water and then applying to an AG-1 X8 100-200 anion exchange resin (Bio-Rad 140-1441). After washing with five column volumes, organic acids were eluted with 3 N HCl and dried under nitrogen gas. Extracts were redissolved in a 1:1 mixture of 75 µl acetonitrile (Regis 270010) and 75 µl N-methyl-N-tert-butyldimethylsilyltrifluoroacetamide (MTBSTFA; Regis 270243) and derivatized for 1 h at 95° C. GC-MS analysis was conducted as described previously (Ward P S, et al. "The common feature of leukemia-associated IDH1 and IDH2 mutations is a neomorphic enzyme activity converting alpha-ketoglutarate to 2-hydroxyglutarate", *Cancer Cell,* 2010, 17:225-234). Isotopic enrichment was assessed by monitoring the abundance of the following ions: m/z 459-465 for citrate, m/z 418-422 for aspartate, m/z 419-423 for malate, m/z 287-291 for fumarate, and m/z 433-438 for 2HG. An explanation for these ions is provided in SI Appendix. Isotopomer distributions were simultaneously corrected for naturally-occurring heavy isotopes of all elements in each mass fragment using a correction matrix as previously described (Weckwerth W. ed. (2007) "*Metabolomics: Methods and Protocols*" (Humana Press, Totowa, N.J.), pp 177-197; Weckwerth W. ed. (2007) "*Metabolomics: Methods and Protocols*", (Humana Press, Totowa, N.J.), pp 177-197), and as detailed in SI Appendix.

Medium glucose, glutamine, and lactate were analyzed using the Nova Biomedical Flex Metabolite Analyzer. Medium metabolite levels were compared with the measured levels in control medium not exposed to cells and then normalized to cell number to arrive at metabolite consumption/production values.

Student's T test was used to calculate final P values.

Example 2

Cancer Cells can Proliferate at 0.5% O2 Despite a Sharp Decline in Glucose-Dependent Citrate Synthesis At 21% O2, cancer cells have been shown to synthesize citrate by condensing glucose-derived acetyl-CoA with glutamine-derived oxaloacetate through the activity of the canonical TCA cycle enzyme citrate synthase (DeBerardinis R J, et al. (2007) "Beyond aerobic glycolysis: Transformed cells can engage in glutamine metabolism that exceeds the requirement for protein and nucleotide synthesis", *Proc Natl Acad Sci USA* 104:19345-19350). In contrast, less is known regarding the synthesis of citrate by hypoxic cells. The glioblastoma cell line SF188 is able to proliferate at 0.5% O2 (FIG. 1A), a level of hypoxia sufficient to stabilize HIF1α (FIG. 1B).

Consistent with previous observations in hypoxic cells, it was found that SF188 cells demonstrated increased lactate production when incubated in hypoxia (FIG. 1C), and the ratio of lactate produced to glucose consumed increased demonstrating an increase in the rate of anaerobic glycolysis. When glucose-derived carbon in the form of pyruvate is converted to lactate, it is diverted away from subsequent metabolism that can contribute to citrate production. However, it was observed that SF188 cells incubated in hypoxia maintain their intracellular citrate to approximately 75% of the level maintained under normoxia (FIG. 1D). This prompted an investigation of how proliferating cells maintain citrate production under hypoxia.

Increased glucose uptake and glycolytic metabolism are critical elements of the metabolic response to hypoxia. To evaluate the contributions made by glucose to the citrate pool under normoxia or hypoxia, SF188 cells incubated in normoxia or hypoxia were cultured in medium containing 10 mM [U-$^{13}$C]glucose. Following a 4 h labeling period, cellular metabolites were extracted and analyzed for isotopic enrichment by gas chromatography-mass spectrometry (GC-MS). In normoxia, the major $^{13}$C-enriched citrate species found was citrate enriched with two $^{13}$C atoms (cit+2), which can arise from the NAD+-dependent decarboxylation of pyruvate+3 to acetyl-CoA+2 by PDH, followed by the condensation of acetyl-CoA+2 with unenriched oxaloacetate (FIG. 1 E-F). Compared with the accumulation of cit+2, we observed minimal accumulation of cit+3 and cit+5 under normoxia. Cit+3 arises from pyruvate carboxylase (PC) dependent conversion of pyruvate+3 to oxaloacetate+3, followed by the condensation of oxaloacetate+3 with unenriched acetyl-CoA. Cit+5 arises when PC-generated oxaloacetate+3 condenses with PDH-generated acetyl-CoA+2. The lack of cit+3 and cit+5 accumulation is consistent with PC activity not playing a major role in citrate production in normoxic SF188 cells, as previously reported (DeBerardinis R J, et al. "Beyond aerobic glycolysis: Transformed cells can engage in glutamine metabolism that exceeds the requirement for protein and nucleotide synthesis", *Proc Natl Acad Sci USA*, 2007, 104:19345-19350). In hypoxic cells, the major citrate species observed was unenriched. Cit+2, cit+3, and cit+5 all constituted minor fractions of the total citrate pool, consistent with glucose carbon not being incorporated into citrate through either PDH or PC-mediated metabolism under hypoxic conditions (FIG. 1F). These data demonstrate that in contrast to normoxic cells, where a large percentage of citrate production depends on glucose-derived carbon, hypoxic cells significantly reduce their rate of citrate production from glucose.

Example 3

Glutamine Carbon Metabolism is Required for Viability in Hypoxia

In addition to glucose, it has been previously reported that glutamine can contribute to citrate production during cell growth under normoxic conditions (DeBerardinis R J, et al. (2007), supra). Surprisingly, under hypoxic conditions it was observed that SF188 cells retained their high rate of glutamine consumption (FIG. 2A). Moreover, hypoxic cells cultured in glutamine-deficient medium displayed a significant loss of viability (FIG. 2B). In normoxia, the requirement for glutamine to maintain viability of SF188 cells can be satisfied by α-ketoglutarate, the downstream metabolite of glutamine that is devoid of nitrogenous groups (Wise D R, et al., "Myc regulates a transcriptional program that stimulates mitochondrial glutaminolysis and leads to glutamine addiction" *Proc Natl Acad Sci USA*, 2008, 105:18782-18787). α-ketoglutarate cannot fulfill glutamine's roles as a nitrogen source for nonessential amino acid synthesis or as an amide donor for nucleotide or hexosamine synthesis, but can be metabolized through the oxidative TCA cycle to regenerate oxaloacetate, and subsequently condense with glucose-derived acetyl-CoA to produce citrate. To test whether the restoration of carbon from glutamine metabolism in the form of α-ketoglutarate could rescue the viability defect of glutamine-starved SF188 cells even under hypoxia, SF188 cells incubated in hypoxia were cultured in glutamine-deficient medium supplemented with a cell-penetrating form of α-ketoglutarate (dimethyl α-ketoglutarate). The addition of dimethyl α-ketoglutarate rescued the defect in cell viability observed upon glutamine withdrawal (FIG. 2B).

These data demonstrated that even under hypoxic conditions, when the ability of glutamine to replenish oxaloacetate through oxidative TCA cycle metabolism is diminished, SF188 cells retain their requirement for glutamine as the carbon backbone for α-ketoglutarate. This result raised the possibility that glutamine could be the carbon source for citrate production through an alternative, non-oxidative, pathway in hypoxia.

Example 4

Figure 2:
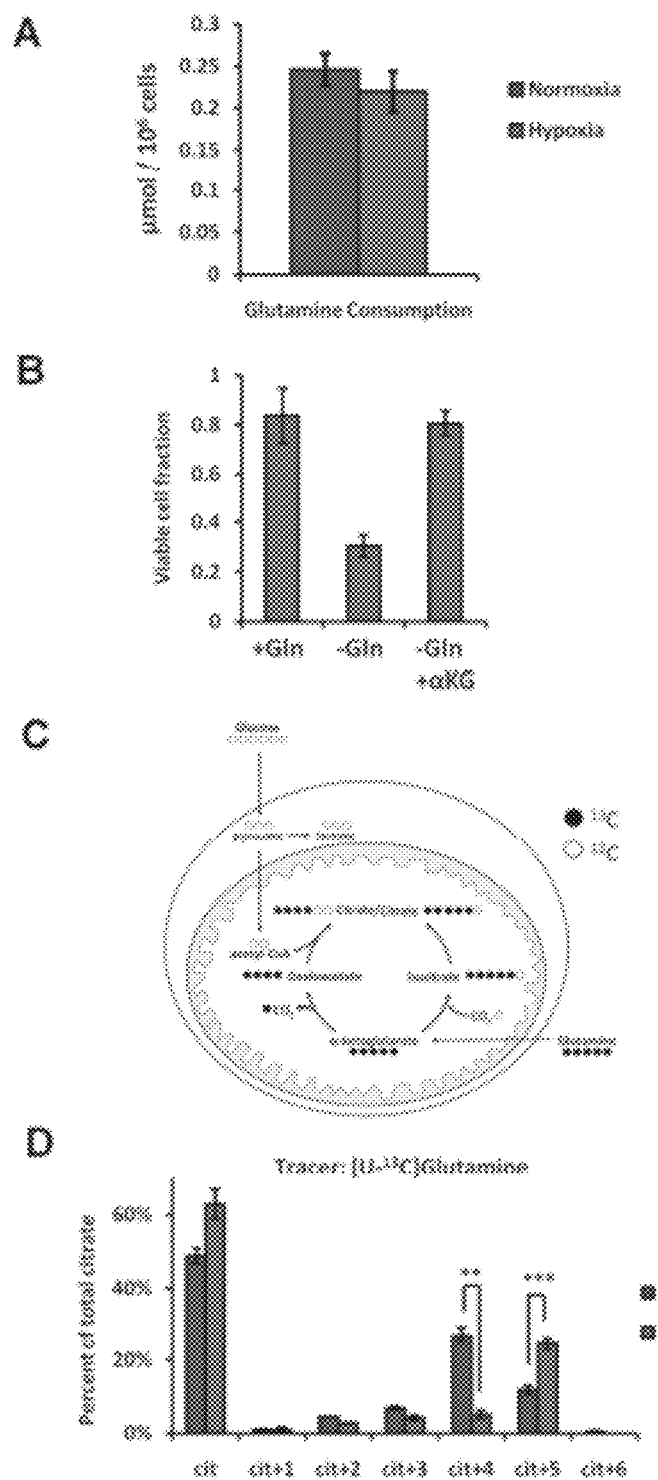
FIG. 2 shows that glutamine carbon is required for hypoxic cell viability and contributes to increased citrate production through reductive carboxylation relative to oxidative metabolism in hypoxia.

Cells Proliferating in Hypoxia Preferentially Produce Citrate Through Reductive Carboxylation Rather than Oxidative Metabolism To distinguish the pathways by which glutamine carbon contributes to citrate production in normoxia and hypoxia, SF188 cells were incubated in normoxia or hypoxia and cultured in medium containing 4 mM [U-$^{13}$C]glutamine. After 4 h of labeling, intracellular metabolites were extracted and analyzed by GC-MS. In normoxia, the cit+4 pool constituted the majority of the enriched citrate in the cell. Cit+4 arises from the oxidative metabolism of glutamine-derived α-ketoglutarate+5 to oxaloacetate+4 and its subsequent condensation with unenriched, glucose-derived acetyl-CoA (FIG. 2 C-D). Cit+5 constituted a significantly smaller pool than cit+4 in normoxia. Conversely, in hypoxia cit+5 constituted the majority of the enriched citrate in the cell. Cit+5 arises from the reductive carboxylation of glutamine-derived α-ketoglutarate+5 to isocitrate+5, followed by the isomerization of isocitrate+5 to cit+5 by aconitase. The contribution of cit+4 to the total citrate pool was significantly lower in hypoxia than normoxia, and the accumulation of other enriched citrate species in hypoxia remained low. These surprising and unexpected data support the role of glutamine as a carbon source for citrate production in normoxia and hypoxia, but through divergent metabolic pathways. In normoxia, oxidative metabolism of glutamine-derived α-ketoglutarate produces oxaloacetate, which can then condense with glucose-derived acetyl-CoA to generate citrate. In hypoxia, there is a relative increase in citrate that is generated independently of glucose via the reductive carboxylation of glutamine-derived α-ketoglutarate to isocitrate and subsequent isomerization to citrate.

Example 5

Figure 3:
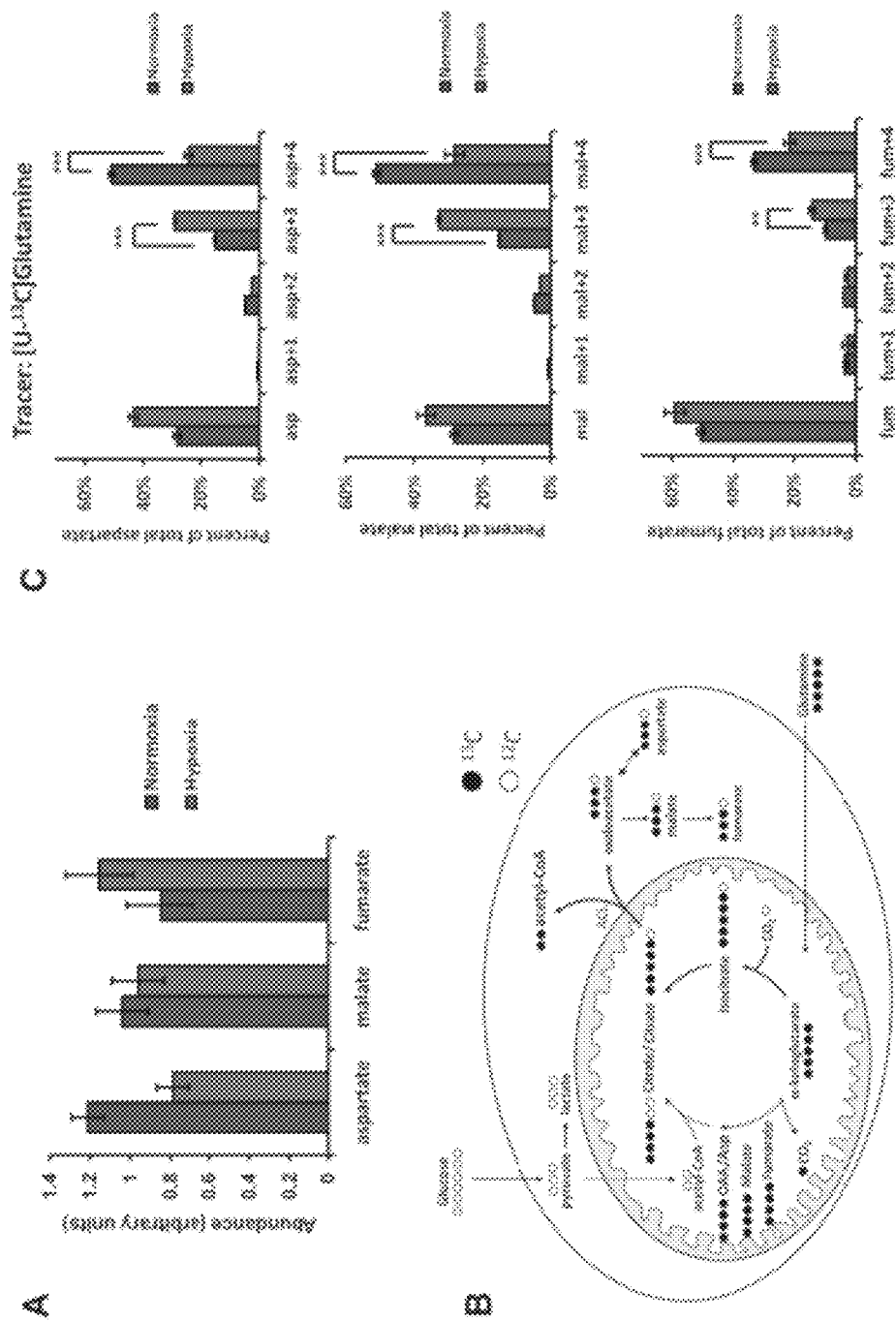
FIG. 3 shows that cancer cells maintain production of other metabolites in addition to citrate through reductive carboxylation in hypoxia.

Hypoxic Cells Maintain Other Metabolite Levels Through Reductive Carboxylation Previous work has documented that in normoxic conditions, SF188 cells use glutamine as the primary anaplerotic substrate, maintaining the pool sizes of TCA cycle intermediates through oxidative metabolism (DeBerardinis R J, et al. (2007), supra). Surprisingly, it has been found that when incubated in hypoxia, SF188 cells largely maintained their levels of aspartate (in equilibrium with oxaloacetate), malate, and fumarate (FIG. 3A). To distinguish how glutamine carbon contributes to these metabolites in normoxia and hypoxia, SF188 cells incubated in normoxia or hypoxia were cultured in medium containing 4 mM [U-$^{13}$C]glutamine. After a 4 h labeling period, metabolites were extracted and the intracellular pools of aspartate, malate, and fumarate were analyzed by GC-MS. In normoxia, the majority of the enriched intracellular asparatate, malate, and fumarate were the +4 species, which arise through oxidative metabolism of glutamine-derived α-ketoglutarate (FIG. 3 B-C). The +3 species, which can be derived from the citrate generated by the reductive carboxylation of glutamine-derived α-ketoglutarate, constituted a significantly lower percentage of the total aspartate, malate, and fumarate pools. By contrast, in hypoxia the +3 species unexpectedly constituted a larger percentage of the total aspartate, malate, and fumarate pools than they did in normoxia. These data demonstrate that in addition to citrate, hypoxic cells preferentially synthesize oxaloacetate, malate, and fumarate through the pathway of reductive carboxylation rather than the oxidative TCA cycle.

Example 6

Figure 4:
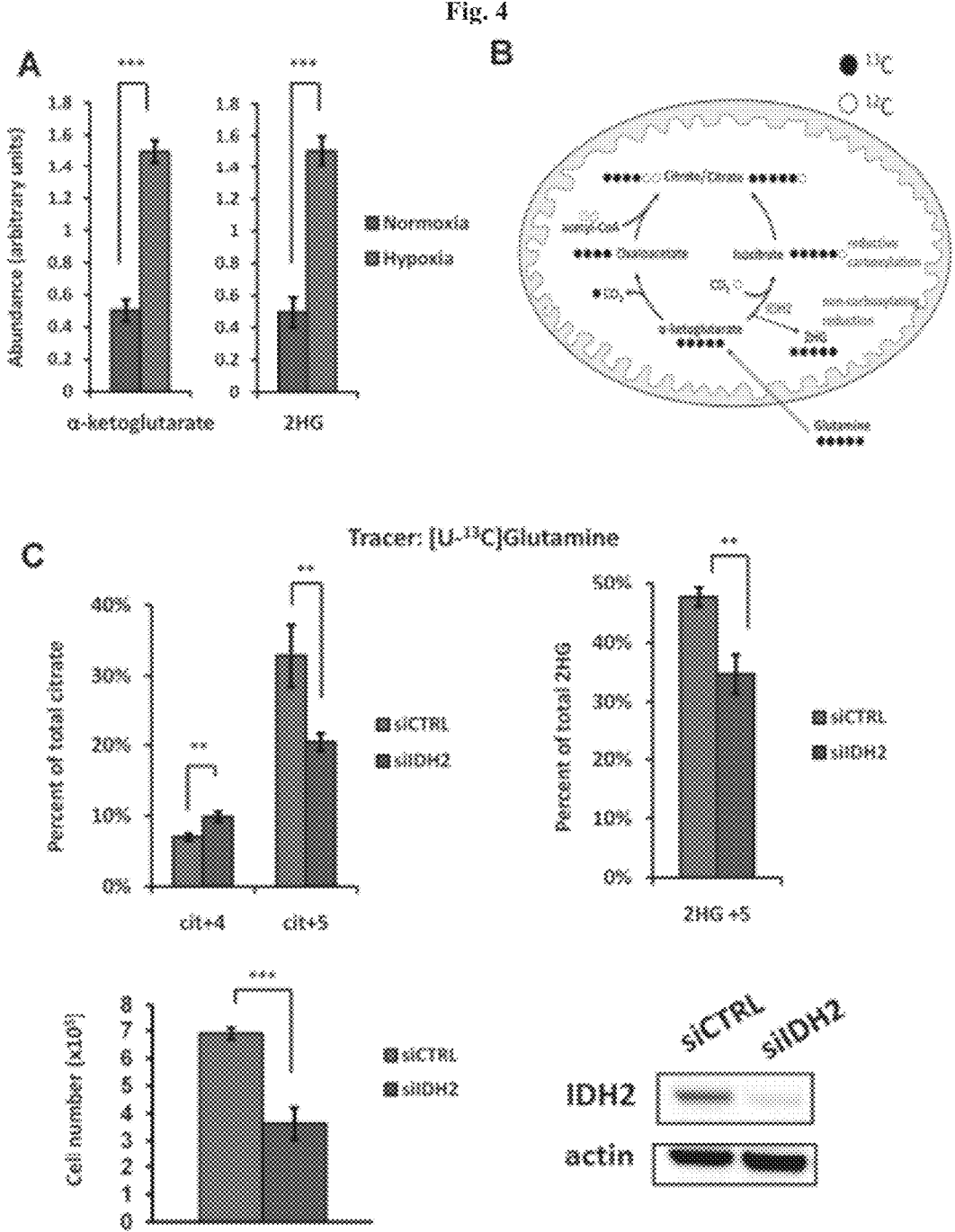
FIG. 4 shows reductive carboxylation of glutamine-derived α-ketoglutarate to citrate in hypoxic cancer cells is dependent on mitochondrial IDH2.

IDH2 is Critical in Hypoxia for Reductive Metabolism of Glutamine and for Cell Proliferation It was further discovered that α-ketoglutarate levels increased in SF188 cells following 24 h in hypoxia (FIG. 4A). Surprisingly, it was also found that levels of the closely related metabolite 2-hydroxyglutarate (2HG) increased in hypoxia, concomitant with the increase in α-ketoglutarate under these conditions. 2HG can arise from the non-carboxylating reduction of α-ketoglutarate (FIG. 4B). Recent work has found that specific cancer-associated mutations in the active sites of either IDH1 or IDH2 lead to a 10-100 fold enhancement in this activity facilitating 2HG production (see Dang L., et al., "Cancer-associated IDH1 mutations produce 2-hydroxyglutarate", Nature, 2009, 462:739-744; Ward P. S., et al. (2010), supra; and Ward P. S., et al. "Identification of additional IDH mutations associated with oncometabolite R(−)-2-hydroxyglutarate production", Oncogene, 2011, Epub 26 Sep. 2011). However, SF188 cells lack IDH1/2 mutations. It was hypothesized that both the increased reductive carboxylation of glutamine-derived α-ketoglutarate to citrate and the increased 2HG accumulation observed in chronic hypoxia could arise from increased reductive metabolism by wild-type IDH2 in the mitochondria.

In an experiment to test this hypothesis, SF188 cells were transfected with either siRNA directed against mitochondrial IDH2 (siIDH2) or non-targeting control, incubated in hypoxia for 2 days, and then cultured for another 4 h in hypoxia in media containing 4 mM [U-$^{13}$C]glutamine. After the labeling period, metabolites were extracted and analyzed by GC-MS (FIG. 4C). Hypoxic SF188 cells transfected with siIDH2 displayed a decreased contribution of cit+5 to the total citrate pool, supporting an important role for IDH2 in the reductive carboxylation of glutamine-derived α-ketoglutarate in hypoxic conditions. The contribution of cit+4 to the total citrate pool did not decrease with siIDH2 treatment, consistent with IDH2 knockdown specifically affecting the pathway of reductive carboxylation but not other fundamental TCA cycle-regulating processes. In confirmation of reverse flux occurring through IDH2, the contribution of 2HG+5 to the total 2HG pool decreased in siIDH2-treated cells. Supporting the importance of citrate production by IDH2-mediated reductive carboxylation for hypoxic cell proliferation, siIDH2-transfected SF188 cells displayed a defect in cellular accumulation in hypoxia. Reduced expression of IDH2 protein following siIDH2 transfection was confirmed by Western blot. Collectively, these data point to the importance of IDH2 for the increase in reductive carboxylation flux of glutamine-derived α-ketoglutarate to maintain citrate levels in hypoxia, and to the importance of this reductive pathway for chronically hypoxic cell proliferation.

Example 7

Figure 5:
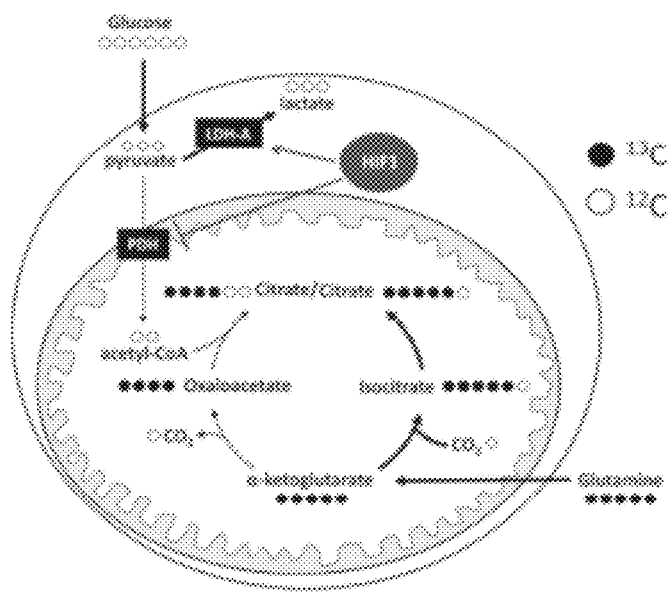
FIG. 5 shows reprogramming of metabolism by HIF1 in the absence of hypoxia is sufficient to induce reductive carboxylation of glutamine-derived α-ketoglutarate.
Figure 5:
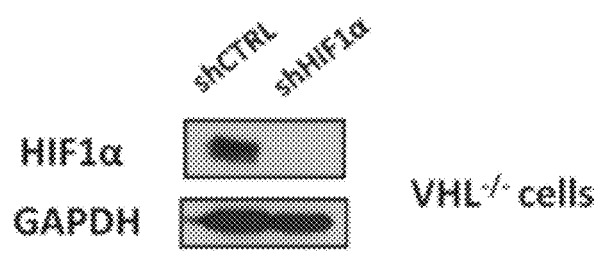
Figure 5:
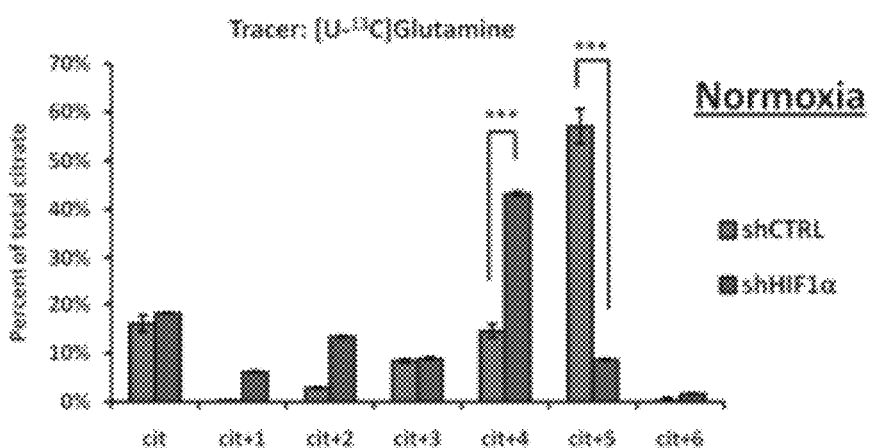

Reprogramming of Metabolism by HIF1 in the Absence of Hypoxia is Sufficient to Induce Increased Citrate Synthesis by Reductive Carboxylation Relative to Oxidative Metabolism The relative increase in the reductive metabolism of glutamine-derived α-ketoglutarate in hypoxia could simply have reflected a decreased ability to carry out oxidative metabolism due to insufficient NAD+, the supply of which can be compromised in hypoxia. Alternatively, the shift to preferential reductive glutamine metabolism in hypoxia could result from the active reprogramming of cellular metabolism by HIF1 (see Kim J-w, et al., "HIF-1-mediated expression of pyruvate dehydrogenase kinase: A metabolic switch required for cellular adaptation to hypoxia", Cell Metab, 2006, 3:177; Papandreou I., et al., "HIF-1 mediates adaptation to hypoxia by actively downregulating mitochondrial oxygen consumption", Cell Metab., 2006, 3:187; and Lum J. J., et al., "The transcription factor HIF-1alpha plays a critical role in the growth factor-dependent regulation of both aerobic and anaerobic glycolysis", Genes Dev, 2007, 21:1037-1049). In short, HIF1 inhibits the generation of mitochondrial acetyl-CoA necessary for the synthesis of citrate by oxidative glucose and glutamine metabolism (FIG. 5A). Notably, SF188 cells incubated in hypoxia displayed the stabilization of HIF1α (FIG. 1B).

To better understand the role of HIF1 in reductive glutamine metabolism, VHL-deficient RCC4 cells were used, which display constitutive expression of HIF1α under normoxia (FIG. 5B). RCC4 cells expressing either a non-targeting control shRNA (shCTRL) or an shRNA directed at HIF1α (shHIF1α) were incubated in normoxia and cultured in medium with 4 mM [U-$^{13}$C]glutamine. Following a 4 h labeling period, metabolites were extracted and the cellular citrate pool was analyzed by GC-MS. In shCTRL cells, which have constitutive HIF1α expression despite incubation in normoxia, the majority of the total citrate pool was constituted by the cit+5 species, with low levels of all other species including cit+4, indicating that reductive carboxylation was responsible for the majority of citrate production (FIG. 5C). By contrast, in HIF1α-deficient cells the contribution of cit+5 to the total citrate pool was greatly decreased, while the contribution of cit+4 to the total citrate pool increased and was the most abundant citrate species. These data demonstrate that the relative enhancement of the reductive carboxylation pathway for citrate synthesis observed in hypoxic cells can be recapitulated by constitutive HIF1 activation.

Example 8

Summary of Data

Compared with glucose metabolism, much less is known regarding how glutamine metabolism is altered under chronic hypoxia. It has also remained unclear how hypoxic cells can maintain the citrate production necessary for macromolecular biosynthesis. The present disclosure demonstrates that in contrast to cells at 21% $O_2$ (normoxic), where citrate is predominantly synthesized through oxidative metabolism of both glucose and glutamine, reductive carboxylation of glutamine carbon becomes the major pathway of citrate synthesis in hypoxia. Moreover, it has been shown that in chronically hypoxic cells, reductive carboxylation of glutamine-derived α-ketoglutarate is dependent on IDH2 and results in a significant increase in the production of 2HG.

The examples above also show that IDH2-mediated reductive carboxylation of glutamine-derived α-ketoglutarate to citrate is an important feature of cells proliferating in hypoxia, and that the reliance on this reductive pathway can be recapitulated in normoxia by constitutive HIF1 activation. The mitochondrial NADPH/NADP+ ratio required to fuel the reductive reaction through IDH2 can arise from the increased NADH/NAD+ ratio existing in the mitochondria under hypoxic conditions, with the transfer of electrons from NADH to NADP+ to generate NADPH occurring through the activity of the mitochondrial transhydrogenase.

In further support of the increased reductive metabolism of glutamine-derived α-ketoglutarate during chronic hypoxia, the example above demonstrates that chronic hypoxia can also lead to elevated 2HG production from wild-type IDH2 in cells lacking IDH1/2 mutations. Thus, 2HG can serve as a cellular or serum biomarker for tissues undergoing chronic hypoxia and/or excessive glutamine metabolism.

Many glucose metabolism alterations in hypoxia are not merely passive responses to the paucity of $O_2$ as an electron acceptor for mitochondrial electron transport. Rather, they can result from active metabolic reprogramming by HIF1. HIF1 promotes LDH-A expression to divert glucose carbon away from mitochondrial metabolism. HIF1 also promotes pyruvate dehydrogenase kinase 1 expression, which leads to phosphorylation and inhibition of PDH activity and a further decline in the contribution of glucose carbon to mitochondrial acetyl-CoA and citrate synthesis. These activities of HIF1 have been understood as enhancing glycolytic ATP production and, in hypoxia, minimizing ROS accumulation by blocking glucose carbon oxidation in the TCA cycle when the resulting electron transport would exceed the cell's ability to assimilate electron flux with $O_2$. However, these explanations do not address how citrate synthesis can be maintained when HIF1 activation diverts glucose carbon away from the mitochondria. Moreover, they do not address whether glutamine metabolism is altered in response to HIF1 activity and, if so, whether this regulation acts to diminish the oxidative metabolism of glutamine.

The IDH2-dependent reductive carboxylation pathway demonstrated here allows for continued citrate production from glutamine carbon when HIF1 activation prevents glucose carbon from contributing to citrate synthesis. Moreover, as opposed to continued oxidative TCA cycle functioning in hypoxia, which increases ROS, reductive carboxylation of α-ketoglutarate in the mitochondria may serve as an electron sink that decreases the generation of ROS. HIF1 activity is not limited to the setting of hypoxia, as a common feature of several cancers is the normoxic stabilization of HIF1α through loss of the VHL tumor suppressor or other mechanisms.

EQUIVALENTS

Those skilled in the art will recognize, or be able to ascertain using no more than routine experimentation, that while the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim. For example, any claim that is dependent on another claim can be modified to include one or more limitations found in any other claim that is dependent on the same base claim.

Where elements are presented as lists, e.g., in Markush group format, it is to be understood that each subgroup of the elements is also disclosed, and any element(s) can be removed from the group. It should it be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not been specifically set forth in haec verba herein. It is noted that the term "comprising" is intended to be open and permits the inclusion of additional elements or steps.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any targeting moiety, any disease, disorder, and/or condition, any method of administration, any therapeutic application, etc.) can be excluded from any one or more claims, for any reason, whether or not related to the existence of prior art.

Publications discussed above and throughout the text are provided solely for their disclosure prior to the filing date of the present application. Nothing herein is to be construed as an admission that the inventors are not entitled to antedate such disclosure by virtue of prior disclosure.

Thus, although the invention has been described in detail with particular reference to these preferred embodiments, other embodiments can achieve the same results. Variations and modifications of the present invention will be obvious to those skilled in the art and it is intended to cover all such modifications and equivalents. The entire disclosures of all references, applications, patents, and publications cited above and/or in the attachments, and of the corresponding application(s), are hereby incorporated by reference.

What is claimed is:

1. A method of treating a subject with low blood oxygen content as indicated by in vitro or in vivo atmospheric oxygen tension of approximately 0.5%, the method comprising a step of:

measuring a level of 2-hydroxyglutarate produced by wild-type IDH2 in a sample from the subject, wherein the level of 2-hydroxyglutarate is elevated at least two-fold in the sample compared to a control level derived from a population of normoxic subjects, wherein the subject does not have a neomorphic gain-of-function mutation in IDH1, does not have a neomorphic gain-of-function mutation in IDH2, and does not have a loss-of-function mutation in 2-hydroxyglutarate dehydrogenase; and administering a treatment comprising supplemental oxygen therapy to the subject.

2. The method of claim 1, wherein the level of 2-hydroxyglutarate is elevated at least three-fold.

3. The method of claim 1, further comprising a step of measuring the level of 2-hydroxyglutarate in a similar sample from the subject after the step of administering.

4. The method of claim 3, wherein the treatment reduces the level of 2-hydroxyglutarate by at least one-fold compared to pretreatment levels.

5. The method of claim 3, wherein the treatment reduces the level of 2-hydroxyglutarate by at least two-fold compared to pretreatment levels.

6. The method of claim 1, wherein the level of 2-hydroxyglutarate is measured by gas chromatography-mass spectrometry, liquid chromatography-mass spectrometry or enzymatic assay.

7. The method of claim 1, wherein the sample is a blood, plasma, serum, or urine sample.

* * * * *